US007658928B2

(12) United States Patent
Fritz et al.

(10) Patent No.: US 7,658,928 B2
(45) Date of Patent: Feb. 9, 2010

(54) METHOD OF VACCINATION COMPRISING ADMINISTERING AN ANTIGEN AND A CATHELICIDIN DERIVED ANTIMICROBIAL PEPTIDE

(75) Inventors: Jörg Fritz, Vienna (AT); Frank Mattner, Vienna (AT); Wolfgang Zauner, Vienna (AT); Michael Buschle, Perchtoldsdorf (AT); Alena Egyed, Vienna (AT)

(73) Assignee: Intercell AG, Vienna (AT)

( * ) Notice: Subject to any disclaimer, the term of this patent is extended or adjusted under 35 U.S.C. 154(b) by 0 days.

(21) Appl. No.: 11/947,729

(22) Filed: Nov. 29, 2007

(65) Prior Publication Data

US 2008/0166368 A1    Jul. 10, 2008

Related U.S. Application Data

(62) Division of application No. 10/344,709, filed as application No. PCT/EP01/09529 on Aug. 17, 2001, now abandoned.

(30) Foreign Application Priority Data

Aug. 17, 2000 (AT) .............................. A 1416/2000

(51) Int. Cl.
*A61K 39/00* (2006.01)
(52) U.S. Cl. .............. 424/184.1; 424/185.1; 424/278.1; 514/2
(58) Field of Classification Search ........................ None
See application file for complete search history.

(56) References Cited

U.S. PATENT DOCUMENTS

| 6,103,888 | A | 8/2000 | Larrick et al. ............... 536/23.5 |
| 6,335,318 | B1 | 1/2002 | Selsted et al. .................. 514/13 |
| 6,821,519 | B2 | 11/2004 | Day et al. .................. 424/231.1 |
| 2002/0197269 | A1 | 12/2002 | Lingnau et al. ........... 424/185.1 |

FOREIGN PATENT DOCUMENTS

| EP | 0974360 | 1/2000 |
| WO | WO 01/54720 | 8/2001 |

OTHER PUBLICATIONS

Agerberth et al., "Antibacterial components in bronchoalveolar lavage fluid from healthy individuals and sarcoidosis patients," *Am. J. Respir. Crit. Care Med.*, 160:283-290, 1999.
Agerberth et al., "The human antimicrobial and chemotactic peptides LL-37 and α-defensins are expressed by specific lymphocyte and monocyte populations," *Blood*, 96:3086-3093, 2000.
Altfeld et al., "Identification of Dominant Optimal HLA-B60- and HLA-B61-Restricted Cytotoxic T-Lymphocyte (CTL) Epitopes: Rapid Characterization of CTL Responses by Enzyme-Linked Immunospot Assay," *J. Virology*, 74:8541-8549, 2000.
Altschul et al., "Gapped BLAST and PSI-BLAST: a new generation of protein database search programs," *Nucleic Acids Research*, 25:3389-3402, 1997.
Andreu and Rivas, "Animal antimicrobial peptides: an overview," *Biopoly*, 47:415-433, 1998.
Attwood, "Genomics. The Babel of bioinformatics," *Science*, 290:471-473, 2000.
Bagella et al., "cDNA sequences of three sheep myeloid cathelicidins," *FEBS Letters*, 376:225-228, 1995.
Bals et al., "Augmentation of innate host defense by expression of a cathelicidin antimicrobial peptide," *Infection and Immunity*, 67(11):6084-6089, 1999.
Bals et al., "The peptide antibiotic LL-37/hCAP-18 is expressed in epithelia of the human lung where it has broad antimicrobial activity at the airway surface," *Proc. Natl. Acad. Sci., USA*, 95:9541-9546, 1998.
Banchereau and Steinman, "Dendritic cells and the control of immunity," *Nature*, 392:245-252, 1998.
Banchereau et al., "Immunobiology of dendritic cells," *Annu. Rev. Immunol.*, 18:767-811, 2000.
Basak et al., "Histidine-rich human salivary peptides are inhibitors of proprotein convertases furin and PC7 but act as substrates for PC1," *J. Peptide Res.*, 49:596-603, 1997.
Befus et al., "Neutrophil defensins induced histamine secretion from mast cells: mechanisms of action," *J. Immunology*, 163:947-953, 1999.
Berzofsky et al., "Progress on new vaccine strategies against chronic viral infections," *J. Clin. Invest.*, 114:450-462, 2004.
Bloom et al., "Identification of tyrosinase-related protein 2 as a tumor rejection antigen for the B16 melanoma," *J. Exp. Med.*, 185:453-459, 1997.
Boman, "Antibacterial peptides: key components needed in immunity," *Cell*, 65:205-207, 1991.
Boman, "Innate immunity and the normal microflora," *Immunological Reviews*, 173:5-16, 2000.
Bradbury and Smyth, "Peptide amidation," *TIBS*, 16:112-115, 1991.
Brossart and Bevan, "Presentation of exogenous protein antigens on major histocompatability complex class I molecules by dendritic cells: pathway of presentation and regulation by cytokines," *Blood*, 90:1594-1599, 1997.
Buschel et al., "Chemically defined, cell-free cancer vaccines: use of tumor antigen-derived peptides of polyepitope proteins for vaccination," *Gene Therapy and Molecular Biology*, 1:309-321, 1998.
Buschle et al., "Transloading of tumor antigen-derived peptides into antigen-presenting cells," *Proc. Natl. Acad. Sci., USA*, 94:3256-3261, 1997.
Chan and Gallo, "PR-39, a syndecan-inducing antimicrobial peptide, binds and affects p130," *J. Biol. Chem.*, 273:28978-28985, 1998.

(Continued)

*Primary Examiner*—Michael Szperka
*Assistant Examiner*—Yunsoo Kim
(74) *Attorney, Agent, or Firm*—Fulbright & Jaworski LLP

(57) ABSTRACT

Described is a vaccine which comprises at least one antigen and at least one cathelicidin derived antimicrobial peptide or a derivative thereof as well as the use of a cathelicidin derived antimicrobial peptide or a derivative thereof for the preparation of an adjuvant for enhancing the immune response to at least one antigen.

6 Claims, 10 Drawing Sheets

OTHER PUBLICATIONS

Chertov et al., "Identification of defensin-1, defensin-2, and CAP37/Azurocidin as T-cell chemoattractant proteins released from interleukin-8-stimulated neturophils," *J. Biol. Chem.*, 271:2935-2940, 1996.

Cole et al., "Inhibition of neutrophil prevents cathelicidin activation and impairs clearance of bacterial from wounds," *Blood*, 97:297-304, 2001.

Cowland et al., "hCAP-18, a cathelin/pro-bactenecin-like protein of human neutrophil specific granules," *FEBS Letters*, 368:173-176, 1995.

Cox and Coulter, "Adjuvants—a classification and review of their modes of action," *Adjuvants Vaccine*, 15:248-256, 1997.

Del Sal et al., "cDNA cloning of the neutrophil bactericidal peptide indolicidin," *Biochem. Biophys. Res. Comm.*, 187:467-472, 1992.

Ezzell, *NIH Research*, 7:46-49, 1995.

Falla et al., "Mode of action of the antimicrobial peptide indolicidn," *J. Biol. Chem.*, 271:19298-19303, 1996.

Fallarino et al., "Improved efficacy of dendritic cell vaccines and successful immunization with tumor antigen peptide-pulsed peripheral blood mononuclear cells by coadministration of recombinant murine interleukin-12," *Int. J. Cancer*, 80:324-333, 1999.

Frohm et al., "The expression of the gene coding for the antibacterial peptide LL-37 is induced in human keratinocytes during inflammatory disorders," *J. Biol. Chem.*, 272:15258-15263, 1997.

Frohm Nilsson et al., "The human cationic antimicrobial protein (hCAP18), a peptide antibiotic, is widely expressed in human squamous epithelia and colocalizes with interleukin-6," *Infection and Immunity*, 67:2561-2566, 1999.

Gallo et al., "Identification of CRAMP, a cathelin-related antimicrobial peptide expressed in the embryonic and adult mouse," *J. Biol. Chem.*, 272:13088-13093, 1997.

Gallo et al., "Syndecans, cell surface heparan sulfate proteoglycans, are induced by a proline-rich antimicrobial peptide from wounds," *Proc Natl. Acad. Sci.*, USA, 91:11035-11039, 1994.

Ganz and Lehrer, "Antibiotic peptides from higher eukaryotes: biology and applications," *Molecular Medicine Today*, 5:292-297, 1999.

Ganz and Lehrer, "Antimicrobial peptides of leukocytes," *Current Opinion in Hematology*, 4:53-58, 1997.

Ganz and Lehrer, "Antimicrobial peptides of vertebrates," *Current Biology*, 10:41-44, 1998.

Ganz and Lehrer, "Defensins," *Current Opinion in Immunology*, 6:584-589, 1994.

Garcia et al., "Human β-defensin 4: a novel inducible peptide with a specific salt-sensitive spectrum of antimicrobial activity," *FASEB*, 15:1819-1821, 2001.

Gennaro et al., "Biological characterization of a novel mammalian antimicrobial peptide," *Biochimica et aBiophysica Acta*, 1425:361-368, 1998.

Giangaspero et al., "Amphipathic alpha helical antimicrobial peptides: a systematic study of the effects of structural and physical properties on biological activity," *Eur J Biochem*, 268:5589-5560, 2001.

Gough et al., "Antiendotoxin activity of cationic peptide antimicrobial agents," *Infection and Immunity*, 64:4922-4927, 1996.

Goulder et al., "Rapid Definition of Five Novel HLA-A*3002-Restricted Human Immunodeficiency Virus-Specific Cytotoxic T-Lymphocyte Epitopes by Elispot and Intracellular Cytokine Staining Assays," *J. Virology*, 75:1339-1347, 2001.

Gudmundsson and Agerberth, "Neutrophil antibacterial peptides, multifuctional effector molecules in the mammalian immune system," *J. of Immunological Methods*, 232:45-54, 1999.

Gudmundsson et al., "The human gene FALL39 and processing of the cathelin precursor the antibacterial peptide LL-37 in granulocytes," *Eur. J. Biochem.*, 238:325-332, 1996.

Hancock and Diamond, "The role of cationic antimicrobial peptides in innate host defences," *Trends in Microbiology*, 8:402-410, 2000.

Hancock and Scott, "The role of anitmicrobial peptides in animal defenses," *Proc. Natl. Acad. Sci., USA*, 97:8856-8861, 2000.

Hancock, "Host defence (cationic) peptides. What is their future clinical potential?" *Drugs*, 57:569-473, 1999.

Harder et al., "Isolation and characterization of human β-defensin-3, a novel human inducible peptide antibiotic," *JBC Papers*, in Press, Published as Manuscript M008557200, Nov. 20, 2000.

Harding, "Class I MHC presentation of exogenous antigens," *J. Clin. Immunology*, 16:90-97, 1996.

Harding, "Phagocytic processing of antigens for presentation by MHC molecules," *Trends in Cell Biol.*, 5:105-109, 1995.

Harwig et al., "Prophenin-1, an exceptionally proline-rich antimicrobial peptide form porcine leukocytes," *FEBS Letters*, 362:65-69, 1995.

Higazi et al., "Defensin modulates tissue-type plasminogen activator and plasminogen binding to fibrin and endothelial cells," *J. Biol. Chem.*, 271:17650-17655, 1996.

Huang et al., "Role of bone marrow-derived cells in presenting MHC class I-restricted tumor antigens," *Science*, 264:961-965, 1994.

Jaeger et al., "A new primate from the middle eocene of myanmar and the Asian early origin of anthropoids," *Science*, 286:528-525, 1999.

Kenney et al., "Protective immunity using recombinant human IL-12 and alum as adjuvants in a primate model of cutaneous Leishmaniasis," *The Journal of Immunology*, 163:4481-4488, 1999.

Klinman and Nutman, "EPILSPOT Assay to Detect Ctokine-Secreting Murine and Human Cells," *Current Protocols in Immunology*, 10:6.19.1-6.19.8, 1994.

Kreil, "D-amino acids in animal peptides," *Annu. Rev. Biochem.*, 66:337-345, 1997.

Kuby, *Immunology*, 4:449-465, 2000.

Kurts et al., "Constitutive class I-restricted exogenous presentation of self antigens in vivo," *J. Exp. Med.*, 184:923-930, 1996.

Larke et al., "Induction of Human Immunodeficiency Virus Type 1-Specific T Cells by a Bluetongue Virus Tubule-Vectored Vaccine Prime-Recombinanat Modified Virus Ankara Boost Regimen," *J. Virology*, 79:14822-14833, 2005.

Lehrer and Ganz, "Antimicrobial peptides in mammalian and insect host defence," *Current Opinion in Immunology*, 11:23-27, 1999.

Lehrer et al., "Defensin: antimicrobial and cytotoxic peptides of mammalian cells," *Annu,. Rev. Immunol.*, 11:105-128, 1993.

Lillard, Jr. et al., "Mechanisms for induction of acquired host immunity by neutrophil peptide defensins," *Proc. Natl. Acad. Sci., USA*, 96:651-656, 1999.

Lindblad et al., "Adjuvant modulation of immune responses to tuberculosis subunit vaccines," *Infection and Immunity*, 65:623-629, 1997.

Luhrs et al., "Induction of Specific Immune Responses by Polycation-Based Vaccines," *J. Immunol.*, 169:5217-5226, 2002.

Mahoney et al., "Molecular analysis of the sheep cathelin family reveals a novel antimicrobial peptide," *FEBS Letters*, 377:519-522, 1995.

Malm et al., "The human cationic antimicrobial protein (hCAP-18) is expressed in the epithelium of human epididymis, is present in the seminal plasma at high concentrations, and is attached to spermatozoa," *Infection and Immunity*, 68:4297-4302, 2000.

McWilliam et al., "Dendritic cells are recruited into the airway epithelium during the inflammatory response to a broad spectrum of stimuli," *J. Exp. Med.*, 184:2429-2432, 1996.

Metzler et al., "Solution structure of human CTLA-4 and delineation of a CD80/CD86 binding site conserved in CD28," *Nature Structural Biol.*, 4:527-531, 1997.

Mizukawa et al., "Presence of defensin in epithelial langerhans cells adjacent to oral carinomas and precancerous lesions," *Anticancer Res.*, 19:2969-2972, 1999.

Monaco, "A molecular model of MHC class-I-restricted antigen processing," *Immunology Today*, 13:173-179, 1992.

Moron et al., "New tools for antigen delivery to the MHC class I pathway," *Trends in Immunology*, 25:92-97, 2004.

Morrison et al., "Identification of the nonamer peptide from influenza A matrix protein and the role of pockets of HLA-A2 in its recognition by cytotoxic T lymphocytes," *Eur. J. Immunol.*, 22:903-907, 1992.

Murphy, "The molecular biology of leukocyte chemoattractant receptors," *Annu. Rev. Immunol.*, 12:593-633, 1994.

Ngo et al., *Protein Folding Problem and Tertiary Structure Prediction*, 492-494, 1994.

Niyonsaba et al., "Evaluation of the effects of peptide antibiotics human β-defensins-1/-2 and LL-37 on histamine release and prostaglandin $D_2$ production from mast cells," *Eur. J. Immunol.*, 31:1066-1075, 2001.

Parent et al., "Gamma Interferon, Tumor Necrosis Factor Alpha, and Nitric Oxide Synthase 2, Key Elements of Cellular Immunity, Perform Critical Protective Functions during Humoral Defense against Lethal Pulmonary *Yersinia pestis* Infection," *Infection and Immunity*, 74:3381-3386, 2006.

Parmiani et al., "Cancer Immunotherapy With Peptide-Based Vaccines: What Have We Achieved? Where Are We Going?" *J. Natl. Cancer. Institute*, 94:805-818, 2002.

Popsueva et al., "A novel murine cathelin-like protein expressed in bone marrow," *FEBS Letters*, 391:5-8, 1996.

Putsep et al., "Antibacterial peptide from *H. pylori*," *Nature*, 398:671-672, 1999.

Putsep et al., "The origin of cecropins; implications from synthetic peptides derived from ribosomal protein L1," *FEBS Letters*, 451:249-252, 1999.

Romeo et al., "Bovine neutrophil antibiotic peptides and their precursors: structure and role in innate immunity," *Croatica Chemica Acta*, 68:607-614, 1995.

Schijns, "Immunological concepts of vaccines adjuvant activity," *Current Opinion in Immunology*, 12:456-463, 2000.

Schmidt et al., "Cell-free tumor antigen peptide-based cancer vaccines," *Proc. Natl. Acad. Sci., USA*, 94:3262-3267, 1997.

Schonwetter et al., "Epithelial antibodies induced at sites of inflammation," *Science*, 267:1645-1648, 1995.

Scott et al., "An α-helical cationic antimicrobial peptide selectively modulates macrophage responses to lipopolysaccharide and directly alters macrophage gene expression," *J. of Immunology*, 165:3358-3365, 2000.

Scott et al., "Biological properties of structurally related α-helical cationic antimicrobial peptides," *Infection and Immunity*, 67:2005-2009, 1999.

Scott et al., "Interaction of cationic peptides with lipoteichoic acid and gram-positive bacteria," *Infection and Immunity*, 67:6445-6453, 1999.

Selsted et al., "Indolicidin, a novel bactericidal tridecapeptide amide from netrophils," *J. Biol. Chem.*, 267:4292-4295, 1992.

Singh and O'Hagan, "Advances in vaccine adjuvants," *Nature Biotechnology*, 17:1075-1081, 1999.

Skerlavaj et al., "Biological characterization of two novel cathelicidin-derived peptides and identification of structural requirements for their antimicrobial and cell lytic activities," *J. Biol. Chem.*, 271:28375-28381, 1996.

Skolnick and Fetrow, "From genes to protein structure and function: novel applications of computational approaches in the genomic era," *Trends in Biotech.*, 18:34-39, 2000.

Sorensen et al., "Human cathelicidin, hCAP-18, is processed to the antimicrobial peptide LL-37 by extracellular cleavage with proteinase 3," *Blood*, 97:3951-3959, 2001.

Sorensen et al., "The human antibacterial cathelicidin, hCAP-18, is synthesized in myelocytes and metamyelocytes and localized to specific granules in neutrophils," *Blood*, 90:2796-2803, 1997.

Sorensen et al., "The human antibacterial cathelicidin, hCAP-18, is bound to lipoproteins in plasma," *J. Biol. Chem.*, 274:22445-22451, 1999.

Spitler, "Cancer vaccines: the interferon analogy," *Cancer Biotherapy*, 10:1-3, 1995.

Steinman, "The dendritic cell system and its role in immunogeicity," *Annu. Rev. Immunol*, 9:271-296, 1991.

Storici et al., "Purification and structural characterization of bovine cathelicidins, precursors of antimicrobial peptides," *Eur. J. Biochem.*, 238:769-776, 1996.

Tani et al., "Defensins act as potent adjuvants that promote cellular and humoral immune responses in mice to a lymphoma idiotype and carrier antigens," *Int. Immunology*, 12:691-700, 2000.

Tossi et al., "Amphipathic, alpha-helical antimicrobial peptides," *Peptide Science*, 55:4-30, 2000.

Travis et al., "Bactericidal activity of mammalian cathelicidin-derived peptides," *Infection and Immunity*, 68:2748-2755, 2000.

Valmori et al., "Functional analysis of two tetanus toxin universal T cell epitopes in their interaction with DR1101 and FR1104 alleles," *J. of Immunology*, 152:2921-2929, 1994.

Van Wetering et al., "Effect of defensins on interleukin-8 synthesis in airway epithelial cells," *Lung Cell. Mol. Physiol.*, 16:L888-L896, 1997.

Van Wetering et al., "Effect of neutrophil serine proteinases and defensins on lung epithelial cells: modulation of cytotoxicity and IL-8 production," *J. Leukocyte Biol.*, 62:217-226, 1997.

Wilson et al., "Antimicrobial peptides in innate intestinal host defence," *Gut*, 47:16-17, 2000.

Wilson et al., "Regulation of intestinal α-defensin activation by the metalloproteinase matrilysin in innate host defense," *Science*, 286:113-117, 1999.

Wu and Hancock, "Interaction of the cyclic antimicrobial cationic peptide bactenecin with the outer and cytoplasmic membrane," *J. Biol. Chem.*, 274:29-35, 1999.

Xiang et al., "An autologous oral DNA vaccine protects against murine melanoma," *Proc. Natl. Acad. Sci. USA*, 97:5492-5497, 2000.

Yang et al., "Differential regulation of formyl peptide receptor-like 1 expression during the differentiation of monocytes to dendritic cells and macrophages," *J. Immunol.*, 166:4092-4098, 2001.

Yang et al., "Human neutrophil defensins selectively chemoattract naïve T and immature dendritic cells," *J. Leukocyte Biol.*, 68:9-14, 2000.

Yang et al., "LL-37, the neutrophil granule- and epithelial cell-derived cathelicidin, utilizes formyl peptide receptor—like 1 (FPRL1) as a receptor to chemoattract human peripheral blood neutrophils, monocytes, and T cells," *J. Exp. Med.*, 192:1069-1074, 2000.

Zanetti et al., "Cathelicidins: a novel protein family with a common proregion and a variable C-terminal antimicrobial domain," *FEBS Letters*, 374:1-5, 1995.

Zanetti et al., "Structure and biology of cathelicidins," In: *The Biology and Pathology of Innate Immunity Mechanisms*, Keisari and Ofek (eds.), 203-218, 2000.

Zanetti et al., "The cathelicidin family of antimicrobial peptide precursors: a component of the oxygen-independent defense mechanisms of neutrophils," *Annals NY Academy of Science*, 832:147-162, 1997.

Zhang et al., "Porcine antimicrobial peptides: new prospects for ancient molecules of host defense," *Vet. Res.*, 31:277-296, 2000.

Zinkernagel et al., "Antigen localisation regulates immune responses in a dose- and time-dependent fashion: a geographical view of immune reactivity," *Immulogical Reviews*, 156:199-209, 1997.

Stills, "Adjuvants and antibody production: dispelling the myths associated with Freund's complete and other adjuvants," *ILAR Journal*, 46(3):280-293, 2005.

```
MCLP          MQFQRDVPSLWLWR-SLSLL-LLLGMGF-SQTPSYRDAVLRAVDDFNQQSLDTNLYRLLDL    58
CATHELIN      ------------------------------QLRYREAVLRAVDRLNEQSSEANLYRLLEL    30
BACTENECIN    METPRASLSLGRWSLWLLLLGLALPSAS-AQALSYREAVLRAVDQLNEQSSEPNIYRLLEL    60
BAC5          METQRASLSLGRCSLWLLLLGLVLPSAS-AQALSYREAVLRAVDQFNERSSEANLYRLLEL    60
INDOLICIDIN   MQTQRASLSLGRWSLWLLLLGLVVPSAS-AQALSYREAVLRAVDQLNELSSEANLYRLLEL    60
CAP18         METHKHGPSLAWWSLLLLLLGLEMPPAI-AQDLTYREAVLRAVDAFNQQSSEANLYRLLSM    60
FALL-39       MKTQRNGHSLGRWSLVLLLLLGLVMPLAIIAQVLSYKEAVLRAIDGINQRSSDANLYRLLDL   61

MCLP          DPEPQGDEDPTPKSVRFRVKETVCGKAERQLPEQCAFKEQGVVKQCMGAVTLNPAADSF     119
CATHELIN      DQPPKADEDPGTPKPVSFTVKETVCPRPTRQPPELCDFKE---KQCVGTVTLNPSIHSL     87
BACTENECIN    DQPPQDEDPDSPKRVSFRVKETVCSRTTQQPPEQCDFKENGLLKRCEGTVTLDQVRGNF    121
BAC5          DPTPNDDLDPGTRKPVSFRVKETDCPRTSQQPLEQCDFKENGLVKQCVGTVTLDPSNDQF   121
INDOLICIDIN   DPPPKDNEDLGTRKPVSFTVKETVCPRTIQQPAEQCDFKEKGRVKQCFKEDGLVKRCVGTVTRYQAWDSF  121
CAP18         DPQQLEDAKPYTPQPVSFTVKETECPRTTWKLPEQCDFKKDGLVKRCMGTVTLNQARGSF   122
FALL-39       DPRPTMDGDPDTPKPVSFTVKETVCPRTTQQSPEDCDFKKDGLVKRCMGTVTLNQARGSF   122

MCLP          DISCNEPGAQPFRFKKISRLAGLLRKGGEKIGEKLKKIGQKIKNFFQKLVPQPEQ-       174
CATHELIN      DISCNEIQSV---------------------------------------------        97
BACTENECIN    DITCNNHQSIRI-TKQPWAPPQAARLCRI--VVIRVCR-----------------       156
BAC5          DINCNELQSVRFRRPPIRPPIRPPFYPPFRPPIRPPIFPPIRPPFRPPLGPFPGRR      177
INDOLICIDIN   DLNCNELQSVILPWKWPWWPWRRG-------------------------------       166
CAP18         DIRCNRAQESPEPTGLRKRL-RK-F--RNKIKEKLKKIGQKIQGFVPKLAPRTDY-      172
FALL-39       DISCDKDNKRFALLGDFFRK-SK-E--KIGKEFKRIVQRIKDELRNLVPRTES---      171
```

Fig.1

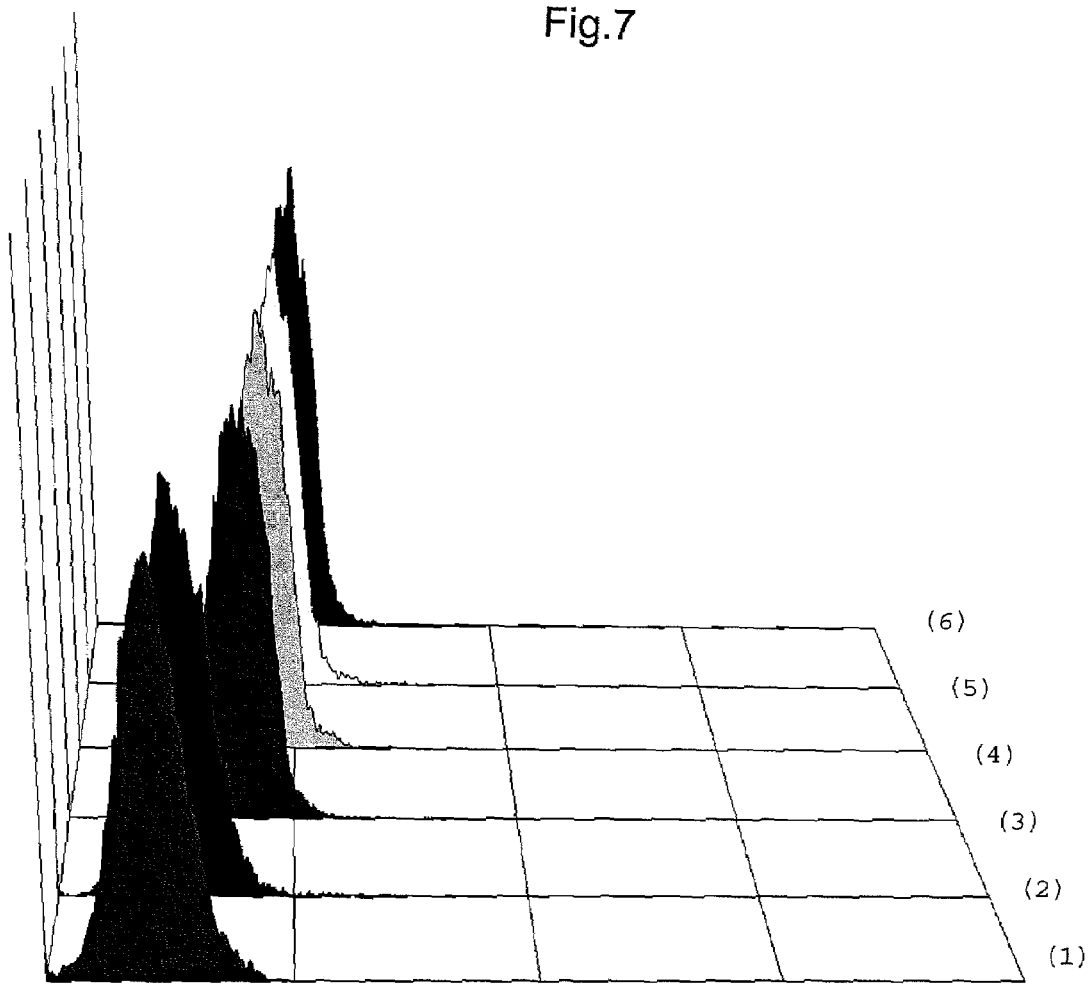

SEQUENCE LISTING

```
<160> NUMBER OF SEQ ID NOS: 25

<210> SEQ ID NO 1
<211> LENGTH: 32
<212> TYPE: PRT
<213> ORGANISM: Artificial Sequence
<220> FEATURE:
```

-continued

```
<223> OTHER INFORMATION: Description of Artificial Sequence:  Synthetic
      peptide

<400> SEQUENCE: 1

Ser Arg Leu Ala Gly Leu Leu Arg Lys Gly Gly Glu Lys Ile Gly Glu
1               5                   10                  15

Lys Leu Lys Lys Ile Gly Gln Lys Ile Lys Asn Phe Phe Gln Lys Leu
            20                  25                  30

<210> SEQ ID NO 2
<211> LENGTH: 37
<212> TYPE: PRT
<213> ORGANISM: Artificial Sequence
<220> FEATURE:
<223> OTHER INFORMATION: Description of Artificial Sequence:  Synthetic
      peptide

<400> SEQUENCE: 2

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: AMIDATION

<400> SEQUENCE: 3

Ile Leu Pro Trp Lys Trp Pro Trp Trp Pro Trp Arg Arg
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence:  Synthetic
      peptide

<400> SEQUENCE: 4

Arg Leu Cys Arg Ile Val Val Ile Arg Val Cys Arg
1               5                   10

<210> SEQ ID NO 5
<211> LENGTH: 173
<212> TYPE: PRT
<213> ORGANISM: Artificial Sequence
<220> FEATURE:
<223> OTHER INFORMATION: Description of Artificial Sequence:  Synthetic
      peptide

<400> SEQUENCE: 5

Met Gln Phe Gln Arg Asp Val Pro Ser Leu Trp Leu Trp Arg Ser Leu
1               5                   10                  15

Ser Leu Leu Leu Leu Leu Gly Met Gly Phe Ser Gln Thr Pro Ser Tyr
            20                  25                  30
```

Arg Asp Ala Val Leu Arg Ala Val Asp Asp Phe Asn Gln Gln Ser Leu
            35                  40                  45

Asp Thr Asn Leu Tyr Arg Leu Leu Asp Leu Asp Pro Glu Pro Gln Gly
        50                  55                  60

Asp Glu Asp Pro Asp Thr Pro Lys Ser Val Arg Phe Arg Val Lys Glu
65                  70                  75                  80

Thr Val Cys Gly Lys Ala Glu Arg Gln Leu Pro Glu Gln Cys Ala Phe
                85                  90                  95

Lys Glu Gln Gly Val Val Lys Gln Cys Met Gly Ala Val Thr Leu Asn
            100                 105                 110

Pro Ala Ala Asp Ser Phe Asp Ile Ser Cys Asn Glu Pro Gly Ala Gln
        115                 120                 125

Pro Phe Arg Phe Lys Lys Ile Ser Arg Leu Ala Gly Leu Leu Arg Lys
    130                 135                 140

Gly Gly Glu Lys Ile Gly Glu Lys Leu Lys Lys Ile Gly Gln Lys Ile
145                 150                 155                 160

Lys Asn Phe Phe Gln Lys Leu Val Pro Gln Pro Glu Gln
                165                 170

<210> SEQ ID NO 6
<211> LENGTH: 96
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Leu Arg Tyr Arg Glu Ala Val Leu Arg Ala Val Asp Arg Leu Asn
1               5                   10                  15

Glu Gln Ser Ser Glu Ala Asn Leu Tyr Arg Leu Leu Glu Leu Asp Gln
            20                  25                  30

Pro Pro Lys Ala Asp Glu Asp Pro Gly Thr Pro Lys Pro Val Ser Phe
        35                  40                  45

Thr Val Lys Glu Thr Val Cys Pro Arg Pro Thr Arg Gln Pro Pro Glu
    50                  55                  60

Leu Cys Asp Phe Lys Glu Lys Gln Cys Val Gly Thr Val Thr Leu Asn
65                  70                  75                  80

Pro Ser Ile His Ser Leu Asp Ile Ser Cys Asn Glu Ile Gln Ser Val
                85                  90                  95

<210> SEQ ID NO 7
<211> LENGTH: 155
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Met Glu Thr Pro Arg Ala Ser Leu Ser Leu Gly Arg Trp Ser Leu Trp
1               5                   10                  15

Leu Leu Leu Leu Gly Leu Ala Leu Pro Ser Ala Ser Ala Gln Ala Leu
            20                  25                  30

Ser Tyr Arg Glu Ala Val Leu Arg Ala Val Asp Gln Leu Asn Glu Gln
        35                  40                  45

Ser Ser Glu Pro Asn Ile Tyr Arg Leu Leu Glu Leu Asp Gln Pro Pro
    50                  55                  60

```
Gln Asp Asp Glu Asp Pro Asp Ser Pro Lys Arg Val Ser Phe Arg Val
 65                  70                  75                  80

Lys Glu Thr Val Cys Ser Arg Thr Thr Gln Gln Pro Pro Glu Gln Cys
                 85                  90                  95

Asp Phe Lys Glu Asn Gly Leu Leu Lys Arg Cys Glu Gly Thr Val Thr
            100                 105                 110

Leu Asp Gln Val Arg Gly Asn Phe Asp Ile Thr Cys Asn Asn His Gln
        115                 120                 125

Ser Ile Arg Ile Thr Lys Gln Pro Trp Ala Pro Gln Ala Ala Arg
130                 135                 140

Leu Cys Arg Ile Val Val Ile Arg Val Cys Arg
145                 150                 155

<210> SEQ ID NO 8
<211> LENGTH: 176
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Met Glu Thr Gln Arg Ala Ser Leu Ser Leu Gly Arg Cys Ser Leu Trp
  1               5                  10                  15

Leu Leu Leu Leu Gly Leu Val Leu Pro Ser Ala Ser Ala Gln Ala Leu
                 20                  25                  30

Ser Tyr Arg Glu Ala Val Leu Arg Ala Val Asp Gln Phe Asn Glu Arg
             35                  40                  45

Ser Ser Glu Ala Asn Leu Tyr Arg Leu Leu Glu Leu Asp Pro Thr Pro
         50                  55                  60

Asn Asp Asp Leu Asp Pro Gly Thr Arg Lys Pro Val Ser Phe Arg Val
 65                  70                  75                  80

Lys Glu Thr Asp Cys Pro Arg Thr Ser Gln Gln Pro Leu Glu Gln Cys
                 85                  90                  95

Asp Phe Lys Glu Asn Gly Leu Val Lys Gln Cys Val Gly Thr Val Thr
            100                 105                 110

Leu Asp Pro Ser Asn Asp Gln Phe Asp Ile Asn Cys Asn Glu Leu Gln
        115                 120                 125

Ser Val Arg Phe Arg Pro Pro Ile Arg Arg Pro Pro Ile Arg Pro Pro
130                 135                 140

Phe Tyr Pro Pro Phe Arg Pro Pro Ile Arg Pro Pro Ile Phe Pro Pro
145                 150                 155                 160

Ile Arg Pro Pro Phe Arg Pro Pro Leu Gly Pro Phe Pro Gly Arg Arg
                165                 170                 175

<210> SEQ ID NO 9
<211> LENGTH: 144
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Met Gln Thr Gln Arg Ala Ser Leu Ser Leu Gly Arg Trp Ser Leu Trp
  1               5                  10                  15

Leu Leu Leu Leu Gly Leu Val Val Pro Ser Ala Ser Ala Gln Ala Leu
                 20                  25                  30
```

Ser Tyr Arg Glu Ala Val Leu Arg Ala Val Asp Gln Leu Asn Glu Leu
          35                  40                  45

Ser Ser Glu Ala Asn Leu Tyr Arg Leu Leu Glu Leu Asp Pro Pro Pro
        50                  55                  60

Lys Asp Asn Glu Asp Leu Gly Thr Arg Lys Pro Val Ser Phe Thr Val
65                  70                  75                  80

Lys Glu Thr Val Cys Pro Arg Thr Ile Gln Gln Pro Ala Glu Gln Cys
                85                  90                  95

Asp Phe Lys Glu Lys Gly Arg Val Lys Gln Cys Val Gly Thr Val Thr
            100                 105                 110

Leu Asp Pro Ser Asn Asp Gln Phe Asp Leu Asn Cys Asn Glu Leu Gln
            115                 120                 125

Ser Val Ile Leu Pro Trp Lys Trp Pro Trp Pro Trp Arg Arg Gly
130                 135                 140

<210> SEQ ID NO 10
<211> LENGTH: 171
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Met Glu Thr His Lys His Gly Pro Ser Leu Ala Trp Trp Ser Leu Leu
1               5                   10                  15

Leu Leu Leu Leu Gly Leu Leu Met Pro Pro Ala Ile Ala Gln Asp Leu
                20                  25                  30

Thr Tyr Arg Glu Ala Val Leu Arg Ala Val Asp Ala Phe Asn Gln Gln
            35                  40                  45

Ser Ser Glu Ala Asn Leu Tyr Arg Leu Leu Ser Met Asp Pro Gln Gln
        50                  55                  60

Leu Glu Asp Ala Lys Pro Tyr Thr Pro Gln Pro Val Ser Phe Thr Val
65                  70                  75                  80

Lys Glu Thr Glu Cys Pro Arg Thr Thr Trp Lys Leu Pro Glu Gln Cys
                85                  90                  95

Asp Phe Lys Glu Asp Gly Leu Val Lys Arg Cys Val Gly Thr Val Thr
            100                 105                 110

Arg Tyr Gln Ala Trp Asp Ser Phe Asp Ile Arg Cys Asn Arg Ala Gln
            115                 120                 125

Glu Ser Pro Glu Pro Thr Gly Leu Arg Lys Arg Leu Arg Lys Phe Arg
130                 135                 140

Asn Lys Ile Lys Glu Lys Leu Lys Lys Ile Gly Gln Lys Ile Gln Gly
145                 150                 155                 160

Phe Val Pro Lys Leu Ala Pro Arg Thr Asp Tyr
                165                 170

<210> SEQ ID NO 11
<211> LENGTH: 170
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Met Lys Thr Gln Arg Asn Gly His Ser Leu Gly Arg Trp Ser Leu Val
1               5                   10                  15

```
Leu Leu Leu Leu Gly Leu Val Met Pro Leu Ala Ile Ile Ala Gln Val
                20                  25                  30

Leu Ser Tyr Lys Glu Ala Val Leu Arg Ala Ile Asp Gly Ile Asn Gln
         35                  40                  45

Arg Ser Ser Asp Ala Asn Leu Tyr Arg Leu Leu Asp Leu Asp Pro Arg
     50                  55                  60

Pro Thr Met Asp Gly Asp Pro Asp Thr Pro Lys Pro Val Ser Phe Thr
 65                  70                  75                  80

Val Lys Glu Thr Val Cys Pro Arg Thr Thr Gln Gln Ser Pro Glu Asp
                 85                  90                  95

Cys Asp Phe Lys Lys Asp Gly Leu Val Lys Arg Cys Met Gly Thr Val
            100                 105                 110

Thr Leu Asn Gln Ala Arg Gly Ser Phe Asp Ile Ser Cys Asp Lys Asp
                115                 120                 125

Asn Lys Arg Phe Ala Leu Leu Gly Asp Phe Phe Arg Lys Ser Lys Glu
130                 135                 140

Lys Ile Gly Lys Glu Phe Lys Arg Ile Val Gln Arg Ile Lys Asp Glu
145                 150                 155                 160

Leu Arg Asn Leu Val Pro Arg Thr Glu Ser
                165                 170

<210> SEQ ID NO 12
<211> LENGTH: 37
<212> TYPE: PRT
<213> ORGANISM: Artificial Sequence
<220> FEATURE:
<223> OTHER INFORMATION: Description of Artificial Sequence:  Synthetic
      peptide

<400> SEQUENCE: 12

Gly Leu Leu Ser Arg Leu Arg Asp Phe Leu Ser Asp Arg Gly Arg Arg
 1               5                  10                  15

Leu Gly Glu Lys Ile Glu Arg Ile Gly Gln Lys Ile Lys Asp Leu Ser
                20                  25                  30

Glu Phe Phe Gln Ser
         35

<210> SEQ ID NO 13
<211> LENGTH: 37
<212> TYPE: PRT
<213> ORGANISM: Artificial Sequence
<220> FEATURE:
<223> OTHER INFORMATION: Description of Artificial Sequence:  Synthetic
      peptide

<400> SEQUENCE: 13

Leu Leu Gly Asp Phe Phe Arg Lys Ser Lys Glu Lys Ile Gly Lys Glu
 1               5                  10                  15

Phe Lys Arg Ile Val Gln Arg Ile Lys Asp Phe Leu Arg Asn Leu Val
                20                  25                  30

Pro Arg Thr Glu Ser
         35

<210> SEQ ID NO 14
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 14

Gly Arg Phe Lys Arg Phe Arg Lys Lys Phe Lys Lys Leu Phe Lys Lys
 1               5                  10                  15

Leu Ser Pro Val Ile Pro Leu Leu His Leu Gly
                20                  25

<210> SEQ ID NO 15
<211> LENGTH: 37
<212> TYPE: PRT
<213> ORGANISM: Artificial Sequence
<220> FEATURE:
<223> OTHER INFORMATION: Description of Artificial Sequence:  Synthetic
      peptide

<400> SEQUENCE: 15

Gly Leu Arg Lys Arg Leu Arg Lys Phe Arg Asn Lys Ile Lys Glu Lys
 1               5                  10                  15

Leu Lys Lys Ile Gly Gln Lys Ile Gln Gly Phe Val Pro Lys Leu Ala
                20                  25                  30

Pro Arg Thr Asp Tyr
         35

<210> SEQ ID NO 16
<211> LENGTH: 46
<212> TYPE: PRT
<213> ORGANISM: Artificial Sequence
<220> FEATURE:
<223> OTHER INFORMATION: Description of Artificial Sequence:  Synthetic
      peptide

<400> SEQUENCE: 16

Arg Phe Arg Pro Pro Ile Arg Arg Pro Pro Ile Arg Pro Pro Phe Tyr
 1               5                  10                  15

Pro Pro Phe Arg Pro Pro Ile Arg Pro Pro Ile Phe Pro Pro Ile Arg
                20                  25                  30

Pro Pro Phe Arg Pro Pro Leu Gly Pro Phe Pro Gly Arg Arg
         35                  40                  45

<210> SEQ ID NO 17
<211> LENGTH: 60
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Arg Ile Arg Pro Arg Pro Pro Arg Leu Pro Arg Pro Arg Pro Arg
 1               5                  10                  15

Pro Leu Pro Phe Pro Arg Pro Gly Pro Arg Pro Ile Pro Arg Pro Leu
                20                  25                  30

Pro Phe Pro Arg Pro Gly Pro Arg Pro Ile Pro Arg Pro Leu Pro Phe
         35                  40                  45

Pro Arg Pro Gly Pro Arg Pro Ile Pro Arg Pro Leu
         50                  55                  60

<210> SEQ ID NO 18
<211> LENGTH: 42
<212> TYPE: PRT
<213> ORGANISM: Artificial Sequence
<220> FEATURE:
<223> OTHER INFORMATION: Description of Artificial Sequence:  Synthetic
``` peptide

<400> SEQUENCE: 18

Arg Arg Arg Pro Arg Pro Pro Tyr Leu Pro Arg Pro Arg Pro Pro
1               5                   10                  15

Phe Phe Pro Pro Arg Leu Pro Pro Arg Ile Pro Pro Gly Phe Pro Pro
            20                  25                  30

Arg Phe Pro Pro Arg Phe Pro Gly Lys Arg
        35                  40

<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ile Leu Pro Trp Lys Trp Pro Trp Trp Pro Trp Arg Arg Gly
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Leu Cys Arg Ile Val Val Ile Arg Val Cys Arg
1               5                   10

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Gly Gly Arg Leu Cys Tyr Cys Arg Arg Arg Phe Cys Ile Cys Val
1               5                   10                  15

Gly

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence:  Synthetic
      peptide

<400> SEQUENCE: 22

Leu Phe Glu Ala Ile Glu Gly Phe Ile
1               5

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence:  Synthetic
      peptide

```
<400> SEQUENCE: 23

Gly Ile Leu Gly Phe Val Phe Thr Leu Thr
 1               5                  10

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence:  Synthetic
      peptide

<400> SEQUENCE: 24

Gln Tyr Ile Lys Ala Asn Ser Lys Phe Ile Gly Ile Thr Glu
 1               5                  10

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence:  Synthetic
      peptide

<400> SEQUENCE: 25

Val Tyr Asp Phe Phe Val Trp Leu
 1               5
```

METHOD OF VACCINATION COMPRISING ADMINISTERING AN ANTIGEN AND A CATHELICIDIN DERIVED ANTIMICROBIAL PEPTIDE

This application is a divisional application of U.S. application Ser. No. 10/344,709, filed Oct. 14, 2003, which is a U.S. national phase application under 35 U.S.C. 371 of PCT Application No. PCT/EP01/09529 filed Aug. 17, 2001, which claims priority to Austrian Application No. A 1416/2000 filed Aug. 17, 2000.

The present invention relates to vaccines comprising at least one antigen and an immunostimulating substance.

Host protection from invading pathogens involves cellular and humoral effectors and results from the concerted action of both non-adaptive (innate) and adaptive (acquired) immunity. The latter is based on specific immunological recognition mediated by receptors, is a recent acquisition of the immune system, and is present only in vertebrates. The former evolved before the development of adaptive immunity, consisting of a variety of cells and molecules distributed throughout the organism with the task of keeping potential pathogens under control (Boman 2000) (Zanetti, Gennaro et al. 1997).

B and T lymphocytes are the mediators of acquired antigen specific adaptive immunity, including the development of immunological memory, which is the main goal of creating a successful vaccine (Schijns 2000). Antigen presenting cells (APCs) are highly specialized cells that can process antigens and display their processed fragments on the cell surface together with molecules required for lymphocyte activation. This means that APCs are very important for the initiation of specific immune reactions. The main APCs for T lymphocyte activation are dendritic cells (DCs), macrophages, and B cells, whereas the main APCs for B cells are follicular dendritic cells. In general DCs are the most powerful APCs in terms of initiation of immune responses stimulating quiescent naive and memory B and T lymphocytes (Banchereau, Briere et al. 2000).

The natural task of APCs in the periphery (e.g. DCs or Langerhans cells) is to capture and process antigens, thereby being activated they start to express lymphocyte co-stimulatory molecules, migrate to lymphoid organs, secrete cytokines and present antigens to different populations of lymphocytes, initiating antigen specific immune responses. They not only activate lymphocytes, under certain circumstances, they also tolerize T cells to antigens (Banchereau and Steinman 1998).

Antigen recognition by T lymphocytes is major histocompatibility complex (MHC) restricted. A given T lymphocyte will recognize an antigen only when the peptide is bound to a particular MHC molecule. In general, T lymphocytes are stimulated only in the presence of self MHC molecules, and antigen is recognized only as peptides bound to self MHC molecules. MHC restriction defines T lymphocyte specificity in terms of the antigen recognized and in terms of the MHC molecule that binds its peptide fragment.

Intracellular and extracellular antigens present quite different challenges to the immune system, both in terms of recognition and of appropriate response. Presentation of antigens to T cells is mediated by two distinct classes of molecules—MHC class I (MHC-I) and MHC class II (MHC-II), which utilize distinct antigen processing pathways. Mainly one could distinguish between two major antigen processing pathways that have evolved. Peptides derived from intracellular antigens are presented to CD8$^+$ T cells by MHC class I molecules, which are expressed on virtually all cells, while extracellular antigen-derived peptides are presented to CD4$^+$ T cells by MHC class II molecules (Monaco 1992), (Harding 1995). However there are certain exceptions to this dichotomy. Several studies have shown that peptides generated from endocytosed particulate or soluble proteins are presented on MHC-I molecules in macrophages as well as in dendritic cells (Harding 1996), (Brossart and Bevan 1997). Therefore APCs like dendritic cells sitting in the periphery, exerting high potency to capture and process extracellular antigens and presenting them on MHC-I molecules to T lymphocytes are interesting targets in pulsing them extracellularily with antigens in vitro and in vivo.

The important and unique role of APCs, including stimulating activity on different types of leukocytes, is reflecting their central position as targets for appropriate strategies in developing successful vaccines. Theoretically one way to do so is to enhance or stimulate their natural task, the uptake of antigen(s). Once pulsed with the appropriate antigens the vaccine is directed against, APCs should start to process the taken up antigen(s), thereby being activated, expressing lymphocyte co-stimulatory molecules, migrating to lymphoid organs, secreting cytokines and presenting antigens to different populations of lymphocytes thereby initiating immune responses. Activated T cells generally secrete a number of effector cytokines in a highly regulated fashion, including interleukin 2 (IL-2), interferon-$\gamma$ (IFN-$\gamma$), tumor necrosis factor alpha (TNF-$\alpha$), IL-4, IL-5 and IL-10. The functional detection of cytotoxic T lymphocyte responses to specific antigens (e.g. tumor antigens, in general antigens administered in a vaccine) is commonly monitored by an ELISpot assay (enzyme-linked immunospot assay), a technique analyzing cytokine production at the single cell level. In the present invention an ELISpot assay for the cellular immunity promoting cytokine IFN-$\gamma$ was used to monitor successful peptide specific T cell activation.

It has previously been shown that polycations efficiently enhance the uptake of MHC class I-matched peptides into tumor cells, a peptide or protein pulsing process which was called "TRANSloading". (Buschle, Schmidt et al. 1997). Furthermore we have shown that polycations are able to "TRANSload" peptides or proteins into antigen presenting cells in vivo as well as in vitro (Buschle 1998). In addition, co-injection of a mixture of poly-L-arginine or poly-L-lysine together with an appropriate peptide as a vaccine protects animals from tumor growth in mouse models (Schmidt, Buschle et al. 1997). This chemically defined vaccine is able to induce a high number of antigen/peptide-specific T cells. That was shown to be at least partly attributable to an enhanced uptake of peptides into APCs mediated by the polycation (Buschle 1998) indicating that APCs when pulsed in vivo with antigens can induce T cell mediated immunity to the administered antigen.

As opposed to adaptive immunity, which is characterized by a highly specific but relatively slow response, innate immunity is based on effector mechanisms that are triggered by differences in the structure of microbial components relative to the host. These mechanisms can mount a fairly rapid initial response, which mainly leads to neutralization of the noxious agents. Reactions of innate immunity are the only defense strategy of lower phyla and have been retained in vertebrates as a first line host defense before the adaptive immune system is mobilized.

In higher vertebrates the effector cells of innate immunity are neutrophils, macrophages and natural-killer (NK) cells and probably also dendritic cells (Mizukawa, Sugiyama et al. 1999), whereas the humoral components in this pathway are the complement cascade and a variety of different binding proteins (Boman 2000).

A rapid and effective component of innate immunity is the production of a large variety of microbicidal peptides with a length of between 12 and one hundred amino acid residues. Several hundred different antimicrobial peptides have been isolated from a variety of organisms, ranging from sponges, insects to animals and humans, which points to a widespread distribution of these molecules. Antimicrobial peptides are also produced by bacteria as antagonistic substances against competing organisms.

Main sources of antimicrobial peptides are granules of neutrophils and epithelial cells lining the respiratory, gastrointestinal and genitourinary tracts. In general they are found at those anatomical sites most exposed to microbial invasion, are secreted into internal body fluids or stored in cytoplasmic granules of professional phagocytes (neutrophils) (Ganz and Lehrer 1997), (Ganz and Lehrer 1998), (Lehrer and Ganz 1999), (Gudmundsson and Agerberth 1999).

The aim of the present invention is to provide an adjuvant/"carrier-peptide" which strongly enhances the immune response to a specific co-administered antigen.

A further object of the present invention is to provide an adjuvant/"carrier-peptide" known as a body-own molecule in animals, including humans, in particular mammals, and reducing the risk of mounting an immune response against the given adjuvant/"carrier-peptide" in animals including humans.

These objects are solved by a vaccine which comprises at least one antigen and at least one cathelicidin derived antimicrobial peptide or a derivative thereof.

Antimicrobial peptides can be grouped into five classes based on their known or expected 3D structure (Boman 2000).

The spectrum of organisms susceptible to the microbicidal activity of antimicrobial peptides is broad, including various bacteria (Gram positive & negative), protozoa, fungi and in some cases virus infected cells and tumor cells.

In general each species is equipped with a different array of these peptides that likely represents the outcome of an evolutionary selection dictated by the preferential association of a specific set of microbes with a given species.

All of the antimicrobial peptides known are produced by proteolytic processing from precursor molecules. In addition an important part of the biosynthesis of the effectors are the different forms of post-transcriptional modifications which are of importance to the final function like C-terminal amidation (e.g. indolicidin, PR-39, some beta-defensins (Bradbury and Smyth 1991), D-amino acid substitutions (Kreil 1997) or pyroglutamate blocking of the N-terminus (e.g. attacins and some beta-defensins).

One major family of cationic antimicrobial peptides (CAPs) in animals and humans are cathelicidins (Zanetti, Gennaro et al. 2000). Cathelicidins are derived from myeloid cells and have been identified in several mammalian species. So far, cathelicidins with masses ranging from 16-26 kDa were found to be expressed mainly in myeloid cells of human, mouse, cow, pig, horse, sheep, rabbit and rat. They are made as precursors, in which the highly identical N-terminal pre-prosequences are followed by highly varied C-terminal sequences that correspond to antimicrobial peptides after removal of the prosequence at specific cleavage sites (shown in FIG. 3, out of (Zanetti, Gennaro et al. 1997)).

The prosequences of all these congeners are highly homologous to the sequence of a protein named cathelin, first isolated from porcine leukocytes. Based on the common presence of this highly conserved cathelin-like domain, these precursors have been grouped into a family named cathelicidins.

The cathelin-like preproregion shows a high intra-species identity ranging from 75% for bovine, to complete identity for some of the porcine congeners. Four invariant cysteins clustered in the C-terminal region of the cathelin-like pro-piece are arranged to form two intramolecular disulfide bonds, imposing structural constraints to the molecule. The cathelin-like proregion shows limited homology to the cystatin family, proteins of known thiol protease inhibitory function. This is further supported by the moderate inhibitory effects exerted by several cathelicidins on the activity of the cysteine proteinase cathepsin L on which the acronym cathelin is based. Although a specific function for this prosequence has not been established, the evolutionary pressure exerted towards its conservation suggests it may play an important biological function, such as targeting of the antimicrobial peptides to the granules or aiding their correct proteolytic maturation.

The preproregion of cathelicidins is 128-143 amino acid residues long, including a putative 29-30 residue signal peptide and a propiece of 99-114 residues, while the C-terminal domain is 12-100 residues long. When these propeptides are secreted, they undergo limited proteolysis. In bovine and porcine neutrophils, cathelicidins are liberated by elastase-mediated cleavage (Cole, Shi et al. 2001), while the human cathelicidin hCAP-18 is processed extracellularly to the antimicrobial peptide LL-37 by proteinase 3 (Sorensen, Follin et al. 2001) indicating that the generation of active antimicrobial peptides from common proproteins occurs differently in related species.

Cathelicidins were first found in secondary granules of neutrophils (Gudmundsson, Agerberth et al. 1996), (Gudmundsson and Agerberth 1999). Thus, cathelicidins are released into inflammatory fluids where they are found at relatively high concentrations (Agerberth, Grunewald et al. 1999), (Gudmundsson and Agerberth 1999). The only cathelicidin found in humans so far, the peptide LL-37 (hCAP-18/FALL-39) is expressed in neutrophil granules and is produced by bone marrow and testis (Cowland, Johnsen et al. 1995), (Sorensen, Arnljots et al. 1997). Additionally, LL-37 is constitutively expressed in squamous epithelia of mouth, tongue, esophagus, cervix, and vagina (Frohm Nilsson, Sandstedt et al. 1999), the lung epithelia (Bals, Wang et al. 1998) and the epithelium of the epididymis (Malm, Sorensen et al. 2000). Furthermore, high levels of LL-37 were found in the seminal plasma (Malm, Sorensen et al. 2000). Moreover, LL-37 is induced in keratinocytes of inflamed skin (Frohm, Agerberth et al. 1997), is found in high concentrations in the lipoprotein fraction of plasma (Sorensen, Bratt et al. 1999) and in bronchoalveolar lavage fluid (Agerberth, Grunewald et al. 1999). Recently the expression of LL-37 in NK, γδ T cells, B cells and monocytes/macrophages has been described (Agerberth, Charo et al. 2000).

The mature antimicrobial peptides corresponding to the C-terminus are structurally diverse sequences (shown in FIG. 1, out of (Popsueva, Zinovjeva et al. 1996)) and individual names have been given to them such as:

bovine cathelicidins (Storici, Tossi et al. 1996), (Skerlavaj, Gennaro et al. 1996), (Gennaro, Scocchi et al. 1998): Bac1 (Bactenecin1), Bac5, Bac7, indolicidin, BMAP-27 (bovine myeloid antimicrobial peptide 27) and BMAP-28;

porcine cathelicidins (Harwig, Kokryakov et al. 1995): PR-39 (proline-arginine-rich 39-amino-acid peptide), PMAP-36

(porcine myeloid antimicrobial peptide 36), PMAP-37, PMAP-23, protegrins, and prophenins;

rabbit cathelicidins: CAP18 (cationic antimicrobial protein 18); human cathelicidins (Cowland, Johnsen et al. 1995), (Gudmundsson, Agerberth et al. 1996): hCAP-18/FALL-39/ LL-37 (human antimicrobial protein/C-terminal derived domains are called FALL-39 or LL-37); murine cathelicidins (Gallo, Kim et al. 1997), (Popsueva, Zinovjeva et al. 1996): mCRAMP (murine cathelin-related antimicrobial peptide), MCLP (murine cathelin-like protein); rat cathelicidins: rCRAMP (rat cathelin-related antimicrobial peptide);

sheep cathelicidins (Mahoney, Lee et al. 1995), (Bagella, Scocchi et al. 1995): SMAP29 (sheep myeloid antimicrobial peptide 29) and SMAP34.

Beside cathelicidins there are other families of antimicrobial peptides identified in animals and humans, mainly: cecropins and defensins (Gudmundsson and Agerberth 1999), (Boman 2000).

Defensins are a family of 4-kDa peptides and their activity depends on both their net cationic charge as well as their 3-D structure. Defensins form multimeric voltage-dependent pores that permeabilize microbial membranes (Ganz and Lehrer 1994) (Ganz and Lehrer 1999). Although similar in shape to α-defensins, β-defensins are slightly larger and differ in the placement and connectivity of their six conserved cysteine residues (Ganz and Lehrer 1998).

Human α-defensins (human neutrophil peptides; HNP 1-4) are mainly found in the granules of neutrophils and participate in the killing of phagocytosed microorganisms (Lehrer, Lichtenstein et al. 1993). More recently two members of this family in humans, HD-5 and HD-6 (human α-defensins 5 & 6), were found to be constitutively produced by specialized secretory cells in small intestinal crypts, the Paneth cells. HD-5 is also constitutively produced in the female reproductive tract (Ganz and Lehrer 1999).

Two classes of β-defensins can be defined by comparing their expression patterns. Constitutively expressed β-defensins are the human β-defensin 1 (hBD 1), expressed in epithelia, and the bovine neutrophil β-defensin (BNBD-1-13) (Ganz and Lehrer 1998). In contrast, the expression of β-defensins such as bovine lingual antimicrobial peptide (LAP) (Schonwetter, Stolzenberg et al. 1995), the bovine tracheal antimicrobial peptide (TAP) and its human homolog β-defensin 2 (hBD 2) are upregulated during infectious challenge (Ganz and Lehrer 1998). Inducible expression has also been described for other known human beta-defensins hBD-3 and hBD-4 (Harder, Bartels et al. 2000), (Garcia, Krause et al. 2001).

A further class of antimicrobial peptides are cecropins. They were the first antimicrobial peptides found in animals. Bacteria were shown to induce these compounds in dormant pupae of the giant silk moth *Hyalophora cecropia* (Boman 1991). Their 3D-structure consists of two α-helices with a hinge in between. Cecropins have so far been found in higher insects and a mammalian cecropin has been isolated from pig intestine (Boman 2000). Cecropin-like peptides have been isolated from sponges and from the *Helicobacter pylori* ribosomal protein L1 (Putsep, Branden et al. 1999), (Putsep, Normark et al. 1999).

Given the very high concentrations that have been recorded at sites of inflammation (Hancock and Diamond 2000)(e.g. 300 μg/ml or more in the sputum of cystic fibrosis patients; 20-100 μg/ml in the dorsal tongue: up to 170 μg/ml in the plasma of septic individuals), one might suspect a key role of CAPs to cope with infections. In addition, CAPs are found at mucosal and epithelial surfaces and in the gut, lungs, kidneys and skin. Their induction during inflammation correlates with a primary role in assisting and/or directing inflammatory responses. Indeed, increased levels of CAPs have been observed in a number of clinical and laboratory-induced infectious and inflammatory states (Hancock and Diamond 2000). Recently, a single enzyme necessary for processing of the pre-prodefensins to the active mature form was identified. Genetic inactivation of this single gene (matrilysin; matrix-metalloproteinase-7: MMP-7) completely inhibited production of active defensin, and subsequently a tenfold increase in the susceptibility to infection by orally introduced virulent bacteria was observed (Wilson, Ouellette et al. 1999). Additionally, a wide range of animal studies and early clinical trials have demonstrated that when exogenously added, naturally and non-naturally occurring CAPs protect against local or systemic infection by bacteria and fungi (reviewed in (Hancock and Diamond 2000), (Hancock 1999)).

However, the action of CAPs is not limited to direct killing of microorganisms. Instead, they have a variety of additional activities that have an impact particularly on the quality and effectiveness of immune responses. CAPs have been reported to be involved in:

a.) the initial lysis of bacterial cells to release inflammatory stimuli such as lipopolysaccharides (LPS), lipoteichoic acids (LTA) or CpG (Hancock and Diamond 2000), (Hancock and Scott 2000);

b.) neutralizing LPS and LTA, thus inhibiting the production of TNF-α and IL-6 production by macrophages (=antiseptic activity) (Scott, Rosenberger et al. 2000), (Scott, Yan et al. 1999), (Scott, Gold et al. 1999), (Gough, Hancock et al. 1996);

c.) mast cell degranulation.
Alpha-defensins have been shown to induce histamine release and vasodilation (Befus, Mowat et al. 1999). In addition, hBD-2 and LL-37 but not hBD-1 were shown to induce histamine release and intracellular calcium mobilization in mast cells. Furthermore, hBD-2 but not LL-37 and hBD-1 exerts prostaglandin $D_2$ production in mast cells (Niyonsaba, Someya et al. 2001).

d.) inhibition of fibrinolysis by tissue plasminogen activator, thus reducing the spreading of bacteria (Higazi, Ganz et al. 1996);

e.) tissue/wound repair through promotion of fibroblast chemotaxis and growth (Gallo, Ono et al. 1994), (Chan and Gallo 1998);

f.) inhibition of tissue injury by inhibiting certain proteases such as furin and cathepsin (Basak, Ernst et al. 1997), (Van Wetering, Mannesse-Lazeroms et al. 1997);

g.) inhibiting the release of immunosuppressive cortisol (Hancock and Diamond 2000);

h.) the recruitment of various immune cell populations. α-defensins have been shown to induce IL-8 production in airway epithelial cells, leading to a recruitment of neutrophils (Van Wetering, Mannesse-Lazeroms et al. 1997). In addition it has been reported that α-defensins exert chemotactic activity for naive $CD4^+/CD45RA^+$ and $CD8^+$ T cells, but not for $CD4^+/CD45$ $RO^+$ memory T cells. (Chertov, Michiel et al. 1996), (Yang, Chen et al. 2000). Similarly, α-defensins and β-defensins were shown to have the capacity to induce the migration of monocyte-derived immature dendritic cells but not of monocytes and mature dendritic cells (Yang, Chertov et al. 1999), (Yang, Chen et al. 2000). Furthermore, this chemotactic activity of β-defensins was shown to be mediated by interacting with one of the chemokine receptors, CCR6 (chemokine receptor 6) expressed on immature but not on mature dendritic cells (Yang, Chertov et al. 1999). Cathelicidins like the human LL-37 and the porcine PR-39 were shown to exert chemotactic activity for neutrophils (Agerberth, Charo et al. 2000), (De, Chen et al. 2000). Furthermore, LL-37 exert chemotactic activity for CD4$^+$ T cells but not for CD8$^+$ T cells (Agerberth, Charo et al. 2000), (De, Chen et al. 2000). In addition it has been shown recently, that LL-37 induces chemotaxis of peripheral blood monocytes, neutrophils and CD4$^+$ T cells, utilizing the formyl peptide receptor-like 1 (FPRL1) (De, Chen et al. 2000). However, no chemotactic activity of LL-37 for immature and mature dendritic cells was observed. These findings were supported by the fact that with differentiation of monocytes into immature dendritic cells, FPRL1 expression was abolished (Yang, Chen et al. 2001). However, the expression of FPRL1 was described to be restricted to cells of myeloid origin and has not yet been described for T lymphocytes (Murphy 1994). Thus, exerting chemotactic activity for T lymphocytes and cells of myeloid origin like neutrophils and monocytes, LL-37 might utilize different receptors.

i.) the promotion of acquired systemic immune responses. Intranasal delivery of α-defensins plus ovalbumin (OVA) enhanced OVA-specific serum IgG antibody responses in C57BL/6 mice (Lillard, Boyaka et al. 1999). Furthermore, intraperitoneal administration of keyhole limpet hemocyanin (KLH) adsorbed to the common adjuvant aluminium hydroxide in combination with α-defensins increased the production of KLH-specific antibodies in Balb/c mice. In addition, α-defensins enhanced the antibody response to a syngeneic tumor antigen, lymphoma Ig idiotype and also augmented resistance to tumor challenge (Tani, Murphy et al. 2000).

A variety of activities of diverse CAPs (e.g. defensins, cathelicidins) important for the instruction of adaptive immune responses have been described to date. Common and diverse activities of different CAPs have been figured out. Some clear differences regarding their chemotactic activity for dendritic cells were shown. While α- & β-defensins chemoattract dendritic cells, chemotactic activity of cathelicidins for this specialized cell type is lacking.

Surprisingly within the scope of the present invention it is shown that cathelicidin derived antimicrobial peptides from different species (the bovine indolicidin, the bovine dodecapeptide, the murine mCRAMP and the human LL-37) exert the ability to enhance the uptake of antigens in dendritic cells of mice and men. Furthermore, subcutaneous administration of a tumor antigen in conjunction with a cathelicidin derived antimicrobial peptide markedly enhanced the immune response to the injected tumor antigen.

In the U.S. Pat. No. 5,837,248, where the stimulation of T cells chemotaxis by a defensin peptide is disclosed, it is mentioned that no other T cell chemotactic peptide would be present in neutrophils apart from defensins and CAP37/azurocidin.

However, even if diverse families of antimicrobial peptides are present in the same cell type (e.g. neutrophils, small intestinal paneth cells; (Ganz and Lehrer 1999)) there are important variations existing among these antimicrobial peptides, which means that features of one family will not necessarily occur in the other family. In general, it appears that the variation is not only due to divergence in amino acid sequences, but also applies to the number and abundance of locally expressed gene products coding for antimicrobial peptides. In the light of this variation, it is clear that these effectors are entities that have been conserved through evolution. Most likely the variation of antibacterial peptides reflects the character of their targets: rapid adaptive evolutionary changes with regard to host-microbe interplay.

The induction of an immune response critically depends on the antigen being available in lymphoid organs. There is no response against antigens that do not reach draining lymph nodes (Zinkernagel, Ehl et al. 1997). Thus, initiation of immune responses takes place exclusively in lymphoid organs. There, initial interactions between antigen-loaded APCs with T and/or B cells allow the initiation of the immune cascade (Kurts, Heath et al. 1996).

In view of these considerations, immune responsiveness that is increased may simply be a result of enhanced translocation of vaccine antigen from the peripheral site of injection towards the draining local lymph node. In this process, naturally occurring antigen presenting cells residing in the periphery, such as dendritic cells or Langerhans cells, play a central role (Schijns 2000). They are described as "natural adjuvants" because they reside in most tissues as sentinels ready to capture antigen very efficiently, which induces their migration to secondary lymphoid organs where they are capable in priming naive T and B cells (Steinman 1991). They are rapidly recruited into sites of tissue injury in response to inoculation with live or inactivated viruses or bacteria (McWilliam, Napoli et al. 1996).

Despite the fact that cecropins resemble similar cathelicidin-like structural properties (α-helical conformation), cecropins in contrast to cathelicidins do not show any antigen pulsing capacity (see example). It is surprising that cathelicidin derived antimicrobial peptides have antigen pulsing capacity and therefore immune response stimulating activity. This confirms that different classes of antimicrobial peptides have different functional abilities and that therefore the reported stimulation of T cells chemotaxis by defensin peptides does not indicate for the skilled man in the art that there exists a similar linkage between innate and adaptive immunity.

Thus, cathelicidins and defensins both released at inflamed tissues instruct adaptive immune responses in different ways. While defensins participate by attracting dendritic cells, cathelicidins are the key for the activation of dendritic cells, as shown in the present invention. Therefore, cathelicidins are central components in mediating immune response stimulating activity and therefore constitute highly effective adjuvants for vaccine development.

It has now surprisingly been shown within the course of the present invention that cathelicidin derived antimicrobial peptides or derivatives thereof have immune response stimulating activity and therefore constitute highly effective adjuvants.

In the scope of the present invention a cathelicidin derived antimicrobial peptide is to be understood as the carboxy-terminal antimicrobial peptide (preferentially but not exclusively encoded by the fourth exon of the cathelicidin gene), followed by the cathelin-like preproregion (preferentially but not exclusively encoded by the first three exons of the cathelicidin gene) of cathelicidins, or derivates thereof. The Cathelicidin preproregions share high intra-species identity ranging from 75-87% for bovine and 90-97% identity for porcine preproregions (Zanetti, Gennaro et al. 1995), they also possess high inter-species identity ranging from 51-65% (compared to hCAP-18, with the program blastp; (Altschul, Madden et al. 1997)), thus possessing intra- and inter-species homology. In the light of this known high intra- and inter-species protein sequence identity of cathelicidin preproregions, for the present invention all antimicrobial peptides are being termed cathelicidin derived antimicrobial peptide if they are derived from proteins or protein domains which possess a protein-sequence identity to the cathelicidin preproregion of higher than (≧) 45%, advantageously higher than 60%, preferably higher than 80% and still preferred higher than 90%, thus are the antimicrobial domains of these proteins to be understood as cathelicidin derived antimicrobial peptides.

Examples of cathelicidin derived antimicrobial peptides are e.g. PMAP-37, hCAP18, BMAp-27, CAP18, Bac5, Bac7, PR-39, indolicidin, bovine dodecapeptide, protegrin PG-2, etc.

An antimicrobial peptide is being termed antimicrobial or bactericidal when it shows activity in the minimum inhibitory concentration assay (MIC), a routinely used assay (Gudmundsson and Agerberth 1999), (Boman 2000).

The MIC of a substance for a range of microorganisms is preferably determined by the broth dilution method which is a particularly exact method. Serial dilutions of each substance are done in Luria-Bertani medium in 96 well plates. Each well is inoculated with 10 µl of $10^4$-$10^5$ colony-forming-units/ml of the test organism. The MIC is determined after incubation for 36-48 hours of the plates at 37° C. The MIC is taken as the lowest antibiotic concentration at which growth is inhibited.

In the scope of the present invention a cathelicidin derived antimicrobial peptide is being termed antimicrobial or bactericidal if it exerts a MIC below 500 µM, preferably below 300 µM, still preferred below 200 µM, still preferred in a range of between 0.05 and 160 µM (Travis, Anderson et al. 2000) of the tested substance to Gram positive and/or Gram negative bacteria, fungi or protozoa.

In the scope of the present invention derivatives of the cathelicidin derived antimicrobial peptides comprise for example fragments of cathelicidin derived antimicrobial peptides as well as cathelicidin derived antimicrobial peptides with one or more mutations such as substitution(s), deletion(s), additions), and any modified cathelicidin derived antimicrobial peptides, e.g. salts, esters, etc. Preferably not more than 10% of the amino acids of a given cathelicidin derived antimicrobial peptide according to the present invention shall be substituted, deleted or added. Such mutations are performed according to standard knowledge, e.g. hydrophobic amino acid residues are exchanged by other hydrophobic residues, etc.

A derivative of a cathelicidin derived antimicrobial peptide has to be understood of the cathelicidin molecule as long as the derivative exerts a MIC below 500 µM, preferably below 300 µM, still preferred below 200 µM, still preferred in a range of between 0.05 and 160 µM. The length of the cathelicidin derived antimicrobial peptide or derivative thereof according to the present invention is not critical. It may vary from e.g. five amino acids to the length of a protein comprising such an antimicrobial peptide or derivative thereof, preferably between 10 and 60 amino acids, as long as it exerts the above mentioned MIC. The protein is for example a cathelicidin, e.g. MCLP (murine catheline-like protein), hCAP-18, etc. Preferably, the molecules according to the present invention also exhibit comparable, especially the same or better, chemotactic activities as the naturally occurring cathelicidin derived peptides.

The vaccine comprises at least one cathelicidin derived antimicrobial peptide or a derivative thereof plus at least one antigen the immune response is to be directed against. Of course, the vaccine may comprise two or more antigens depending on the desired immune response. The antigen(s) may also be modified so as to further enhance the immune response.

Preferably, proteins or peptides derived from viral or bacterial pathogens from fungi or parasites, as well as tumor antigens (cancer vaccines) or antigens with a putative role in autoimmune disease are used as (including derivatized antigens like glycosylated, lipidated, glycolipidated or hydroxylated antigens). Furthermore, carbohydrates, lipids or glycolipids may be used as antigens themselves. The derivatization process may include the purification of a specific protein or peptide from the pathogen, the inactivation of the pathogen as well as the proteolytic or chemical derivatization or stabilization of such a protein or peptide. Alternatively, also the pathogen itself may be used as an antigen. The antigens are preferably peptides or proteins, carbohydrates, lipids, glycolipids or mixtures thereof.

Preferably, the antigen is a peptide consisting of 5 to 60, preferably 6 to 30, especially 8 to 11, amino acid residues. Antigens of this length have been proven to be especially suitable for T cell activation. The antigens can further be coupled with a tail according to A 657/2000. Also, the antigen can be coupled, e.g. covalently bound, to the cathelicidin derived antimicrobial peptide. Of course the resulting compound must not be a naturally occurring cathelicidin.

The relative amounts of the ingredients of the present composition are highly dependent on the necessities of the individual composition. Preferably between 10 ng and 1 g of antigen and cathelicidin derived antimicrobial peptide are applied. Preferred amounts of antigen/cathelicidin derived antimicrobial peptide lie in the range of 0.1 to 1000 µg antigen per vaccination and 0.1 to 1000 µg cathelicidin derived antimicrobial peptide.

The composition according to the present invention may further contain auxiliary substances, such as buffers, salts, stabilizers, antioxidants, etc., or other effective substances, such as antiinflammators or antinociceptive drugs.

The present compositions may be applied to a patient, e.g. a vaccination candidate, in efficient amounts, e.g. at weekly, bi-weekly or monthly intervals. Patients to be treated with the present composition may also be vaccinated repeatedly or only once. A preferred use of the present invention is the active immunization, especially of humans or animals without protection against the specific antigen.

The present composition may be applied subcutaneously, intramuscularly, rectally, intravenously, intradermally, intrapinnally, transdermally as well as by oral uptake.

If the vaccine comprises more than one cathelicidin derived antimicrobial peptide or a derivative thereof, these cathelicidin derived antimicrobial peptides will interact with each other so as to enhance the immune response to the antigen(s) even stronger.

Of course, the vaccine according to the present invention can comprise any further substance, as for example any other pharmaceutically acceptable carrier, etc. The vaccine according to the present invention may be formulated according to known methods, e.g. as I.V. vaccines, DNA vaccines, transdermal vaccines, topical vaccines, intranasal vaccines and as combination vaccines. The dosages may be selected by standard processes for vaccines which are improvements of known vaccines, however, a lower dosage than the known vaccine is possible for the same protection and therefore preferred.

Preferably, the vaccine is provided in a storage-stable form, e.g. lyophilized, optionally provided in combination with a suitable reconstitution solution.

Preferably, the cathelicidin is an animal cathelicidin. In the scope of the present invention "animal cathelicidin" includes human cathelicidin, in particular mammalian cathelicidin. Especially if the cathelicidin is from the animal species for which the vaccine is designed, the antimicrobial peptides derived from these cathelicidins will not be recognized by the animal immune system, thus reducing the risk of mounting an immune response against the antimicrobial peptides derived from cathelicidins in that animal.

According to a preferred embodiment the animal cathelicidin is a mouse cathelicidin, the cathelicidin derived antimicrobial peptide preferably comprising a sequence according to Seq. ID 1. If the vaccine is administered to a mouse, the cathelicidin derived antimicrobial peptide will not be recognized and no immune response against the cathelicidin derived antimicrobial peptide will be induced. However, this cathelicidin derived antimicrobial peptide is also suitable for vaccines which will be administered to any other animal, including humans. The cathelicidin derived antimicrobial peptide comprising the sequence according to Seq. ID 1 has been shown to be particularly effective.

According to a preferred embodiment the cathelicidin is a human cathelicidin, the cathelicidin derived antimicrobial peptide preferably comprising a sequence according to Seq. ID 2. If the vaccine is administered to humans, no immune response against the cathelicidin derived antimicrobial peptide will be induced since it will not be recognized by the immune system. The cathelicidin derived antimicrobial peptide comprising a sequence according to Seq. ID 2 has been shown to be particularly effective when added to a vaccine comprising at least one antigen.

According to a preferred embodiment of the present invention the animal cathelicidin derived antimicrobial peptide is an indolicidin peptide, preferably a bovine indolicidin peptide and particularly preferred comprising a sequence according to Seq. ID 3.

In the scientific literature different sequences of bovine indolicidin, with (Del Sal, Storici et al. 1992), (Zanetti, Gennaro et al. 1995), (Zanetti, Gennaro et al. 1997) and without (Selsted, Novotny et al. 1992), (Falla, Karunaratne et al. 1996), (Andreu and Rivas 1998), (Hancock and Diamond 2000) a carboxy-terminal glycine, have been published. The tryptophan-rich bovine indolicidin has been purified from bovine neutrophils as an amidated tridecapeptide (Selsted, Novotny et al. 1992). An additional glycine, not found in purified indolicidin, was found present at the carboxyl terminus of the deduced cDNA sequence, likely being involved in post-translational amidation (Del Sal, Storici et al. 1992). In the present invention, bovine indolicidin is preferably synthesized according to the peptide purified from bovine neutrophils (Selsted, Novotny et al. 1992) comprising the sequence according to SEQ ID No. 3 in its C-terminal aminated form: NH2-ILPWKWPWWPWRR-CONH2. This cathelicidin derived antimicrobial peptide is particularly for vaccines designed for bovines, since no immune response will be induced against the cathelicidin derived antimicrobial peptide in this animal species. However, it is also suitable for vaccines for any other animal species, including humans. The cathelicidin derived antimicrobial peptide comprising a sequence according to Seq. ID 3 has proved to be particularly effective as an adjuvant.

A preferred animal cathelicidin derived antimicrobial peptide is a bovine cyclized and/or linear dodecapeptide comprising a sequence according to Seq. ID 4. Even though this cathelicidin derived antimicrobial peptide is rather short, it has been shown to effectively enhance the immune response against the antigen(s) comprised in the vaccine.

Theoretically a vaccine should contain at least two components: (1) the antigen against which the immune response should be mounted and (2) the adjuvant, which is there to enhance and/or direct the immune response. Immunological adjuvants were originally described as "substances used in combination with a specific antigen that produce more immunity than the antigen alone" (Singh and O'Hagan 1999). It is known that a high diversity of adjuvants regarding their immunostimulatory capacity is given (Schijns 2000). Thus, improved efficacy has been described in combining differentially acting adjuvants for the preparation of vaccines. For example, protective immunity using the recombinant human cytokine IL-12 and aluminium hydroxide in a primate model of cutaneous leishmaniasis was shown (Kenney, Sacks et al. 1999). Furthermore, improved efficacy of dendritic cell vaccines and successful immunization with tumor antigen peptide-pulsed peripheral blood mononuclear cells by coadministration of the recombinant murine cytokine IL-12 was shown (Fallarino, Uyttenhove et al. 1999). But not only cytokines in combination with other adjuvants were shown to synergize. For example dimethyl dioctadecyl ammoniumbromide coadjuvanted with poly(I-C) or the cytokines IFN-γ, IL-2 and IL-12 shows modulating effect of immune responses to tuberculosis subunit vaccines (Lindblad, Elhay et al. 1997).

Preferably, the vaccine comprises at least one further immune response stimulating substance. As immune response stimulating substance any substance or molecule can be used which is known to be active as an adjuvant. Such substances are disclosed in WO93/19768. Other substances may be e.g. polycations, as for example polylysine or polyarginine. Other adjuvants may be components in the form of particles, e.g. silica gel or dextran beads, which are sufficiently small so that they can enter into the cells. The addition of this further immune response stimulating substance will render the vaccine even more efficient.

Preferably, the immune response stimulating substance is a cytokine. Cytokines play an important role in activating and stimulating B cells, T cells and NK cells, macrophages, dendritic cells and various other cells participating in inducing immune responses. Any cytokine can be used which will additionally enhance the immune response to the antigen(s).

Another aspect of the present invention is the use of a cathelicidin derived antimicrobial peptide or a derivative thereof for the preparation of an adjuvant for enhancing the immune response to at least one antigen. Also according to this aspect of the invention "cathelicidin derived antimicrobial peptide", "cathelicidin", "derivative", and "antigen" are to be understood as above defined.

Preferably, the adjuvant enhances the uptake of at least one antigen in antigen presenting cells (APC). Since more antigen is taken up in the antigen presenting cells, the APC-induced cascades leading to the induction of antigen specific immune effector cells, like T cells, are enhanced. Therefore, an enhanced uptake of the antigen in APCs enhances the immune response to these antigens.

Preferably, the cathelicidin is an animal cathelicidin. Particularly preferred are cathelicidins which do not induce an immune response in the individual to which the cathelicidins are administered.

According to a preferred embodiment of the present invention the cathelicidin is a mouse cathelicidin, the cathelicidin derived antimicrobial peptide preferably comprising a sequence according to Seq. ID 1.

According to a further advantageous embodiment the cathelicidin is a human cathelicidin, the cathelicidin derived antimicrobial peptide preferably comprising a sequence according to Seq. ID 2.

Preferably, the cathelicidin derived antimicrobial peptide is an indolicidin peptide, preferably a bovine indolicidin peptide and further preferred a cathelicidin derived antimicrobial peptide comprising a sequence according to Seq. ID 3.

Preferably, the cathelicidin derived antimicrobial peptide is a bovine cyclized and/or linear dodecapeptide comprising a sequence according to Seq. ID 4.

The advantages of these above mentioned cathelicidin derived antimicrobial peptide are the same as mentioned above.

According to a preferred embodiment of the invention, the adjuvant is added to a vaccine. It is of course possible to administer the adjuvant directly to the animal, e.g. preferably before the vaccination. It is, however, easier for the administration to add the adjuvant to a vaccine which is then administered to the animal all at once.

According to a further aspect, the present invention relates to a method of vaccinating an animal including humans against a specific antigen or a group of specific antigens, said method comprising the administration of an effective amount of a vaccine according to the present invention to said animal, including humans, to be vaccinated. Alternatively, the method comprises administering an effective Mount of an adjuvant comprising a cathelicidin derived antimicrobial peptide, after which a vaccine is administered.

The invention will be described in more detail by the following examples and figures, but the invention is of course not limited thereto.

FIG. 1 shows sequence similarities between cathelicidin proteins.

FIG. 7 shows TRANSloading of P388D1 with increasing amounts of cecropin like Hp RPL1 (amino acid residues 2-20) derived antimicrobial peptides as "carrier-peptides".

Figure 8A:
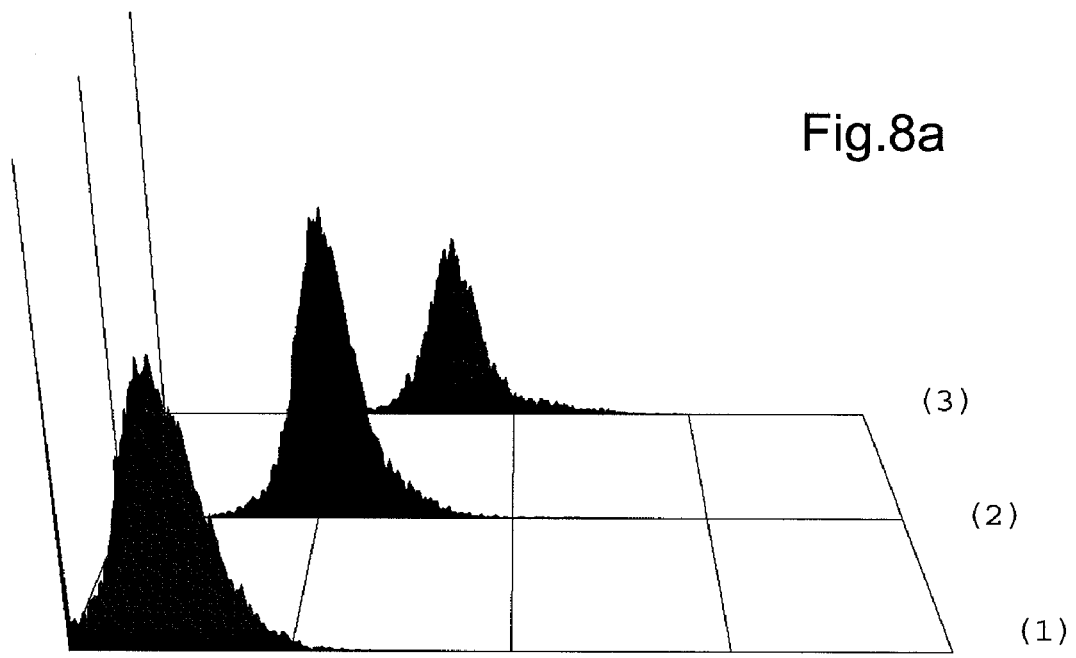
Figure 8B:
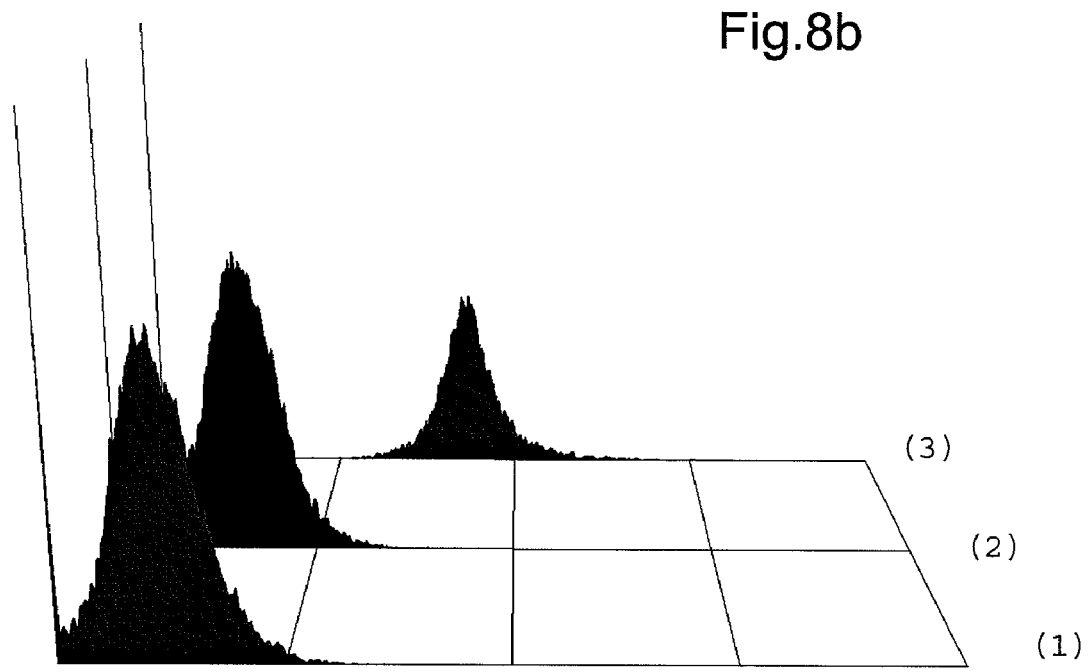

FIG. 8 shows TRANSloading of human DCs with human MHC class I and MHC class II peptides by LL-37. (FIG. 8A) (1) no peptide (cells alone) (2) 2.5 µg FL-GILGFVFTLT (SEQ ID NO:23) (MHC class I; peptide alone) (3) 2.5 µg FL-GILGFVFTLT (SEQ ID NO:23) (MHC class I)+30 µg LL-37 (SEQ ID NO:2). (FIG. 8B) (1) no peptide (cells alone) (2) 2.5 µg FL-QYIKANSKFIGITE (SEQ ID NO:24) (MHC class II; peptide alone) (3) 2.5 µg FL-QYIKANSKFIGITE (SEQ ID NO:24) (MHC class II)+30 µg LL-37 (SEQ ID NO:2).

Figure 9:
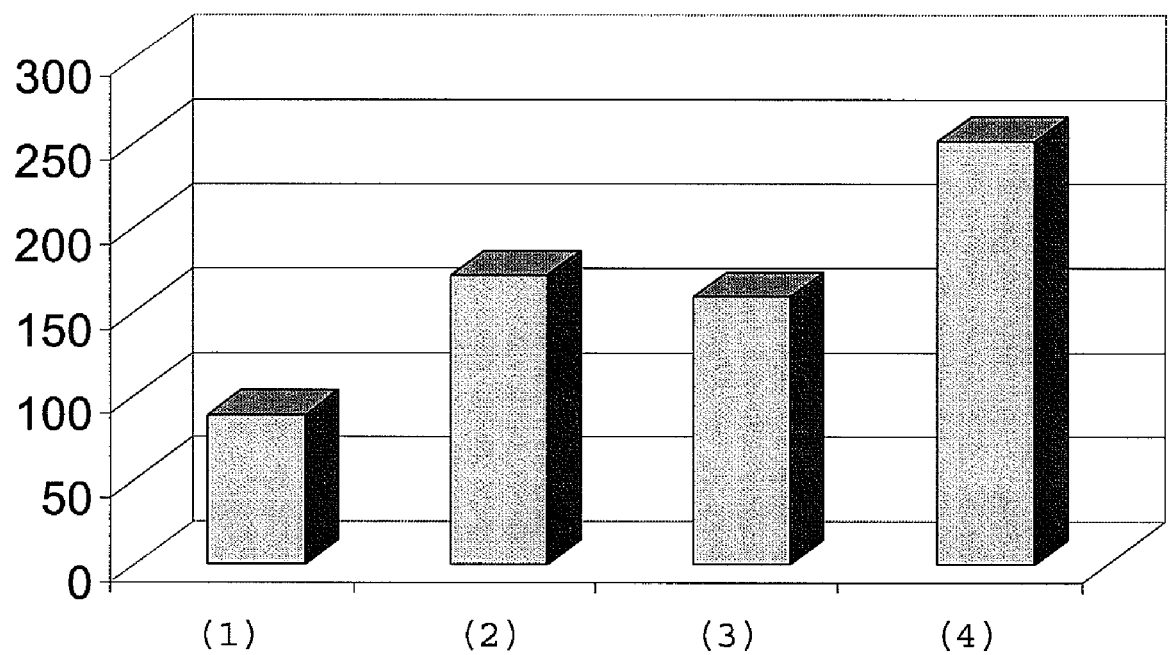
Figure 10:
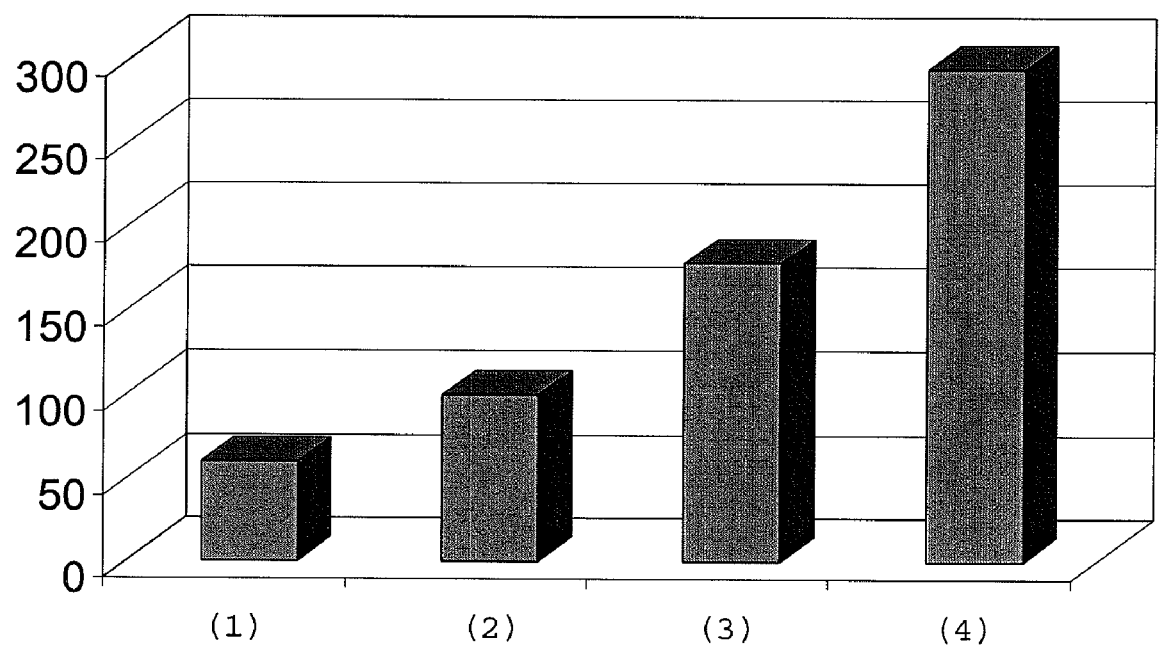

FIGS. 9 and 10 show the amount of IFN-γ-producing cells in vaccinated mice.

In FIG. 1 the similarities of various cathelicidin proteins are shown. The deduced amino acid sequence of MCLP (murine catheline-like protein, SEQ. ID 5) is aligned with the precursor sequence of peptide antibiotics from rabbit (cathelin, SEQ. ID 6, and CAP18, SEQ. ID 7), cow (bactenecin, SEQ. ID 8, Bac5, SEQ. ID 9, indolicidin, SEQ. ID 10), human (FALL-39, SEQ. ID 11). These are examples of cathelicidin derived antimicrobial peptides according to the present invention. Cysteins are boxed. The dibasic protease processing sites are underlined. Alignment was performed using the program DNA-SUN.

Figure 2:
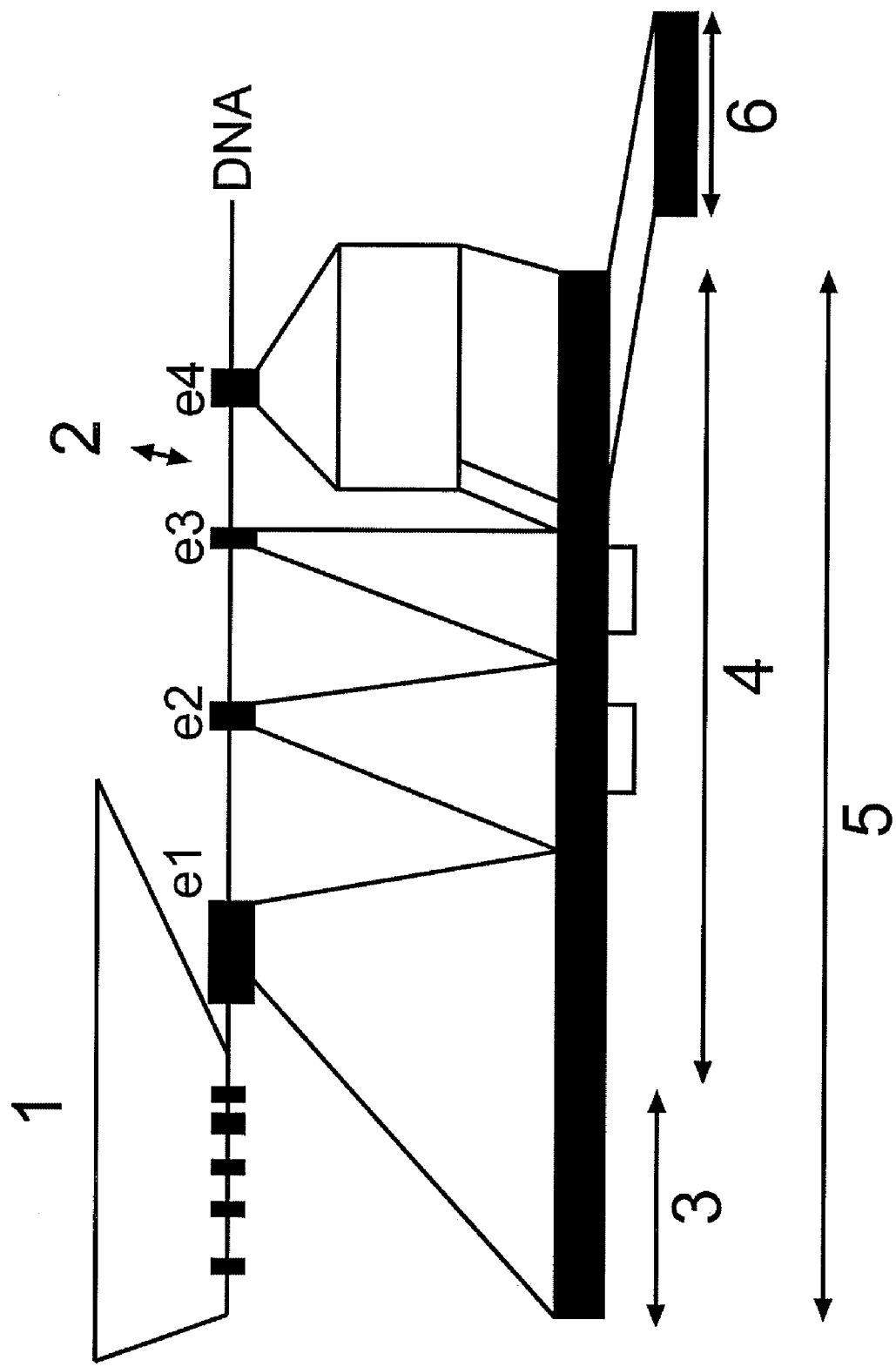
FIG. 2 shows the arrangement for the human gene for proFALL-39/hCAP18.

FIG. 2 shows the arrangement of the human gene for proFALL-39/hCAP18. The overall structure with three conserved exons (e1-e3) is the same for all cathelicidin genes. The variable part is always exon 4, which in human, pig, cow, rabbit, mouse and sheep can code for totally different effectors, belonging to the first four classes of antimicrobial peptides. Region 1 indicates the control sites for transcription factors like NF-KB, NF-IL6, APRF. Arrow 2 indicates the hypothetic site for exon shuffling, region 3 shows the signal peptide, region 4 the cathelin-derived precursor, region 5 the primary translation product. Region 6 indicates the product of exon 4 wherein FALL-39 and LL-37 are the abbreviations for the C-terminal antimicrobial peptides derived from hCAP-18. The processing of FALL-39 has not yet been worked out.

Figure 3:
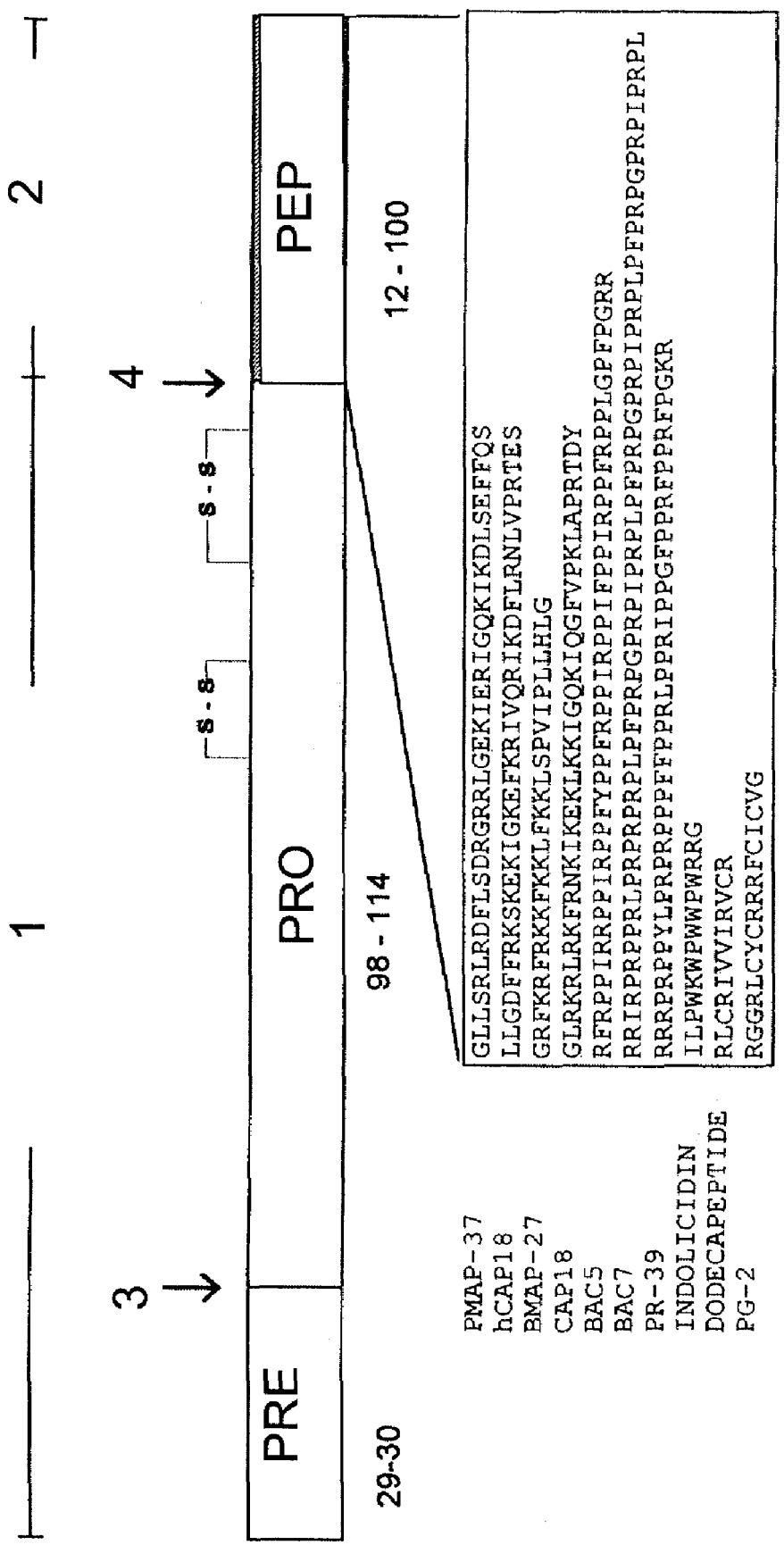
FIG. 3 shows a schematic representation of propeptides of the cathelicidin family.

FIG. 3 shows the schematic representation of propeptides of the cathelicidin family. Some of the C-terminal antimicrobial peptides are shown, representative of α-helical (PMAP-37, SEQ. ID 12; hCAP18, SEQ. ID 13; BMAP-27, SEQ. ID 14; CAP18, SEQ. ID 15), Pro- and Arg-rich (Bac5, SEQ. ID 16; Bac7, SEQ. ID 17; PR-39, SEQ. ID 18), Trp-rich (indolicidin, SEQ. ID 3), one disulfide bridge containing (dodecapeptide, SEQ. ID 4), and two disulfide bridges containing (protegrin PG-2, SEQ. ID 19) sequences. These are examples for cathelicidin derived antimicrobial peptides according to the present invention. Region 1 indicates the conserved pre-proregion, region 2 the variable antimicrobial domain, arrow 3 indicates the site for the signal peptidase, arrow 4 the cleaving site for elastase. The numbers under the three regions (pre, pro, pep(tide)) indicate the number of amino acid residues of the peptides.

EXAMPLES

Test for the Ability of Different Peptides to Enhance the Uptake of a labelled antigenic peptide into APCs (TRANSloading Assay; (Buschle, Schmidt et al. 1997)) and the Induction of Peptide Specific T Cell Responses In Vivo To test if diverse cathelicidin or cecropin derived antimicrobial peptides are able to function as "carrier-peptides" for antigens, to TRANSload APCs in vitro, which means enhancing the antigen uptake into APCs, fluorescent labelled peptides were used as antigenic peptides. They were mixed with diverse types and concentrations of "carrier-peptides" as indicated.

To compare the efficiency of peptide delivery of these diverse "carrier-peptides", the amount of peptide uptake into APCs was monitored by incubating P388D1 cells (murine monocyte-macrophage antigen presenting cell line; purchased from ATCC (TIB-63), or human CD1a positive (derived from human HLA-A2 positive donors, CD14+ positive PBMCS) dendritic cells, for 1 h at 37° C. with a constant amount of fuorescein-tagged peptide alone or in combination with diverse "carrier-peptides" at concentrations indicated. Before analysing the cells by flow cytometry, the cells were washed extensively to remove free peptide. The relative amount of fluorescein-tagged peptide taken up by the cells was measured by flow-cytometry.

Example 1

TRANSloading Murine Macrophages with Cathelicidin Derived Antimicrobial Peptides as "Carrier-Peptides"

Figure 4:
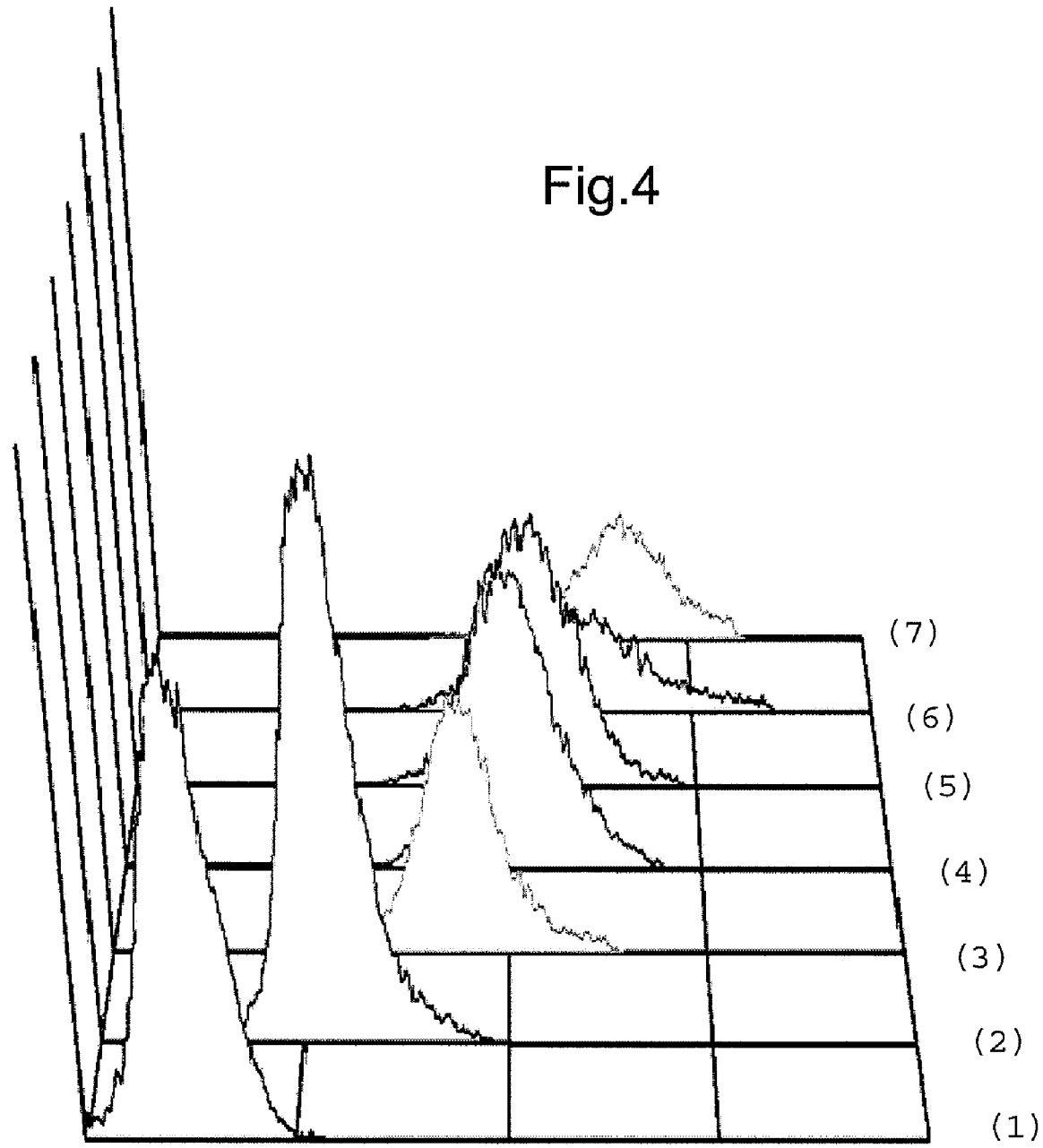
FIG. 4 shows TRANSloading of P388D1 with cathelicidin derived antimicrobial peptides as "carrier-peptides".

Bovine indolicidin (SEQ ID NO:3), linear or cyclized bovine dodecapeptide (SEQ ID NO:4), murine cathelicidin derived antimicrobial peptide (SEQ ID NO:1) were used at concentrations representing an equal amount of positive charges. The antigenic peptide used is an influenza-haemaglutinin derived MHC class I (Kd) binding peptide (Buschle, Schmidt et al. 1997). The amounts of antigenic peptide and carrier-peptides used were as follows (see FIG. 4, fluorescence intensity in log scale):
(1) No peptide (cells alone)
(2) 2 µg FL-LFEAIEGFI (SEQ ID NO:22) (peptide alone)
(3) 2 µg FL-LFEAIEGFI (SEQ ID NO:22)+63 µg bovine indolicidin (SEQ ID NO:3)
(4) 2 µg FL-LFEAIEGFI (SEQ ID NO:22)+75 µg cyclized bovine dodecapeptide (SEQ ID NO:4)
(5) 2 µg FL-LFEAIEGFI (SEQ ID NO:22)+75 µg linear bovine dodecapeptide (SEQ ID NO:4*)
(6) 2 µg FL-LFEAIEGFI (SEQ ID NO:22)+20 µg poly-L-arginine
(7) 2 µg FL-LFEAIEGFI (SEQ ID NO:22)+58 µg murine antimicrobial peptide (SEQ ID NO:1)

Whereas fluorescence appears to be sparse in cells treated with peptide alone, intense fluorescence of "TRANSloaded" cells was found in all cells which were TRANSloaded with cathelicidin derived antimicrobial peptides as "carrier-peptides", indicating that they are able to pulse APCs with antigenic peptides very efficiently. All tested cathelicidin derived antimicrobial peptides greatly enhance the peptide delivery and function as good "carrier-peptide" to APCs.

Example 2

A Comparison of Cecropins and Cathelicidin Derived Antimicrobial Peptides for their TRANSloading Activity Bovine indolicidin (SEQ ID NO:3), linear or cyclized bovine dodecapeptide (SEQ ID NO:4) and cecropin like *Helicobacter pylori* RPL1 derived peptide (Hp RpL1 2-20); amino acid residues 2-20 (Putsep, Normark et al. 1999), (Boman 2000), were used at concentrations representing an equal amount of positive charges. The antigenic peptide used is an influenza-haemagglutinin derived MHC class I (Kd) binding peptide (Buschle, Schmidt et al. 1997). The amounts of antigenic peptide and carrier-peptides used were as follows:
(1) No peptide (cells alone)
(2) 2 µg FL-LFEAIEGFI (SEQ ID NO:22) (peptide alone)
(3) 2 µg FL-LFEAIEGFI (SEQ ID NO:22)+47 µg cecropin like Hp RpL1 2-20
(4) 2 µg FL-LFEAIEGFI (SEQ ID NO:22)+63 µg bovine indolicidin (SEQ ID NO:3)
(5) 2 µg FL-LFEAIEGFI (SEQ ID NO:22)+37.5 µg cyclized bovine dodecapeptide (SEQ ID NO:4)

Figure 5:
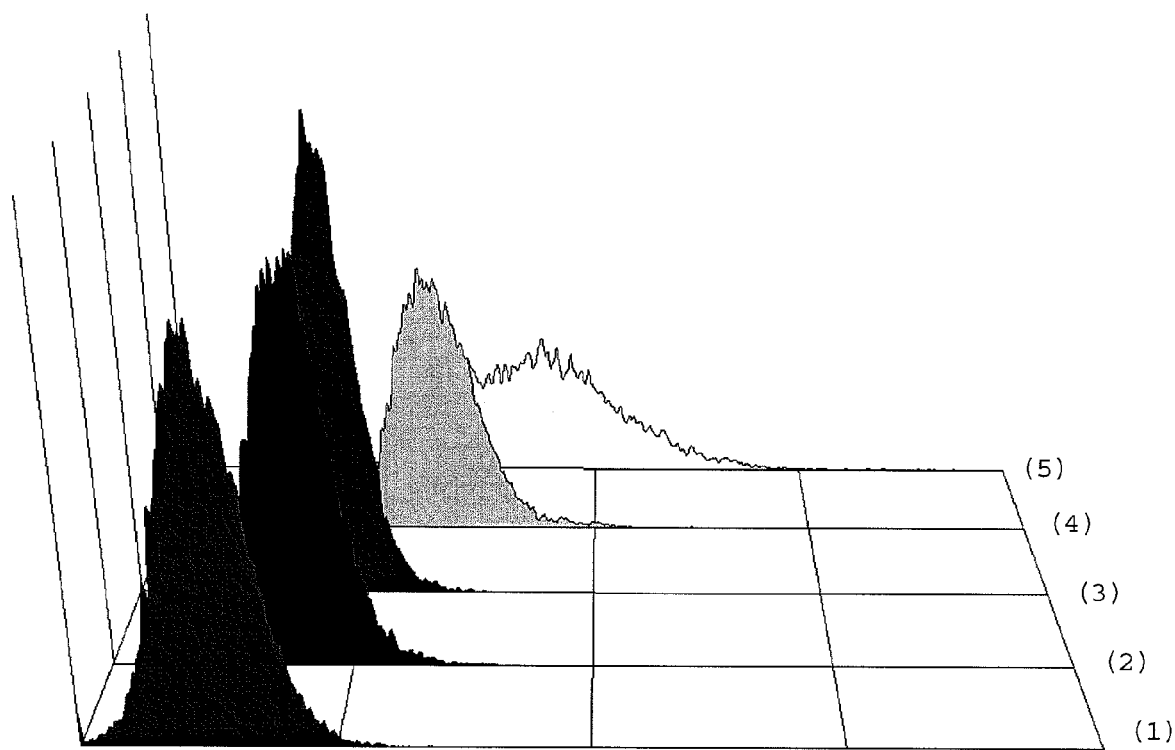
FIG. 5 shows TRANSloading of P388D1 with cecropin or cathelicidin derived antimicrobial peptides as "carrier-peptides".

While cathelicidin derived antimicrobial peptides show clear and significant TRANSloading activity, cecropin derived antimicrobial peptides exert only little enhancement of peptide uptake (s. FIG. 5, fluorescence intensity in log scale).

Example 3

Linear Bovine Dodecapeptide at Increasing Concentrations

The antigenic peptide used is an influenza-hemagglutinin derived MHC class I (Kd) binding peptide (Buschle, Schmidt et al. 1997). The amounts of antigenic peptide and carrier-peptides used were as follows.
(1) No peptide (cells alone)
(2) 2 µg FL-LFEAIEGFI (SEQ ID NO:22) (peptide alone)
(3) 2 µg FL-LFEAIEGFI (SEQ ID NO:22)+18.75 µg lin. bovine dodacapeptide (SEQ ID NO:4)
(4) 2 µg FL-LFEAIEGFI (SEQ ID NO:22)+37.5 µg lin. bovine dodecapeptide (SEQ ID NO:4)
(5) 2 µg FL-LFEAIEGFI (SEQ ID NO:22)+75 µg lin bovine dodecapeptide (SEQ ID NO:4)
(6) 2 µg FL-LFEAIEGFI (SEQ ID NO:22)+150 µg lin bovine dodecapeptide (SEQ ID NO:4)

Figure 6:
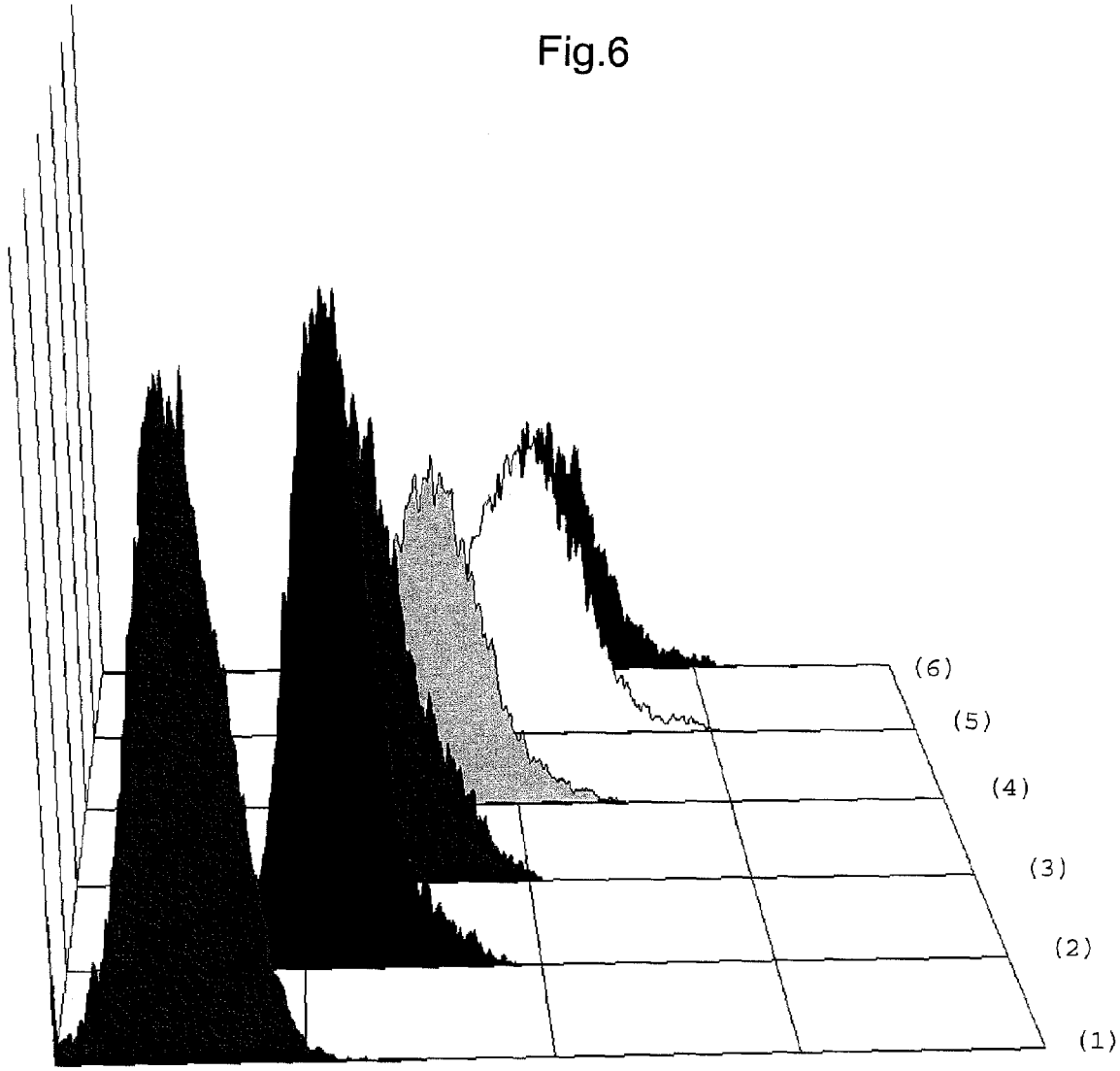
FIG. 6 shows TRANSloading of P388D1 with increasing amounts of cathelicidin derived antimicrobial peptides (bovine linear dodecapeptide SEQ ID 4) as "carrier-peptide".

It was shown (FIG. 6, fluorescence intensity in log scale) that with increasing amounts of cathelicidin derived antimicrobial peptides (bovine dodecapeptide: SEQ ID NO:4) the pulsing effect also increased significantly.

Example 4

Cecropin like Hp RpL1 Derived Antimicrobial Peptide at Increasing Concentrations The antigenic peptide used is an influenza-haemagglutinin derived MHC class I (Kd) binding peptide (Buschle, Schmidt et al. 1997). The amounts of antigenic peptide and carrier-peptides used were as follows (see FIG. 7, fluorescence intensity in log scale).
(1) No peptide (cells alone)
(2) 2 µg FL-LFEAIEGFI (SEQ ID NO:22) (peptide alone)
(3) 2 µg FL-LFEAIEGFI (SEQ ID NO:22)+25 µg cecropin like Hp RpL1 2-20
(4) 2 µg FL-LFEAIEGFI (SEQ ID NO:22)+50 µg cecropin like Hp RpL1 2-b 20
(5) 2 µg FL-LFEAIEGFI (SEQ ID NO:22)+100 µg cecropin like Hp RpL1 2-20
(6) 2 µg FL-LFEAIEGFI (SEQ ID NO:22)+200 µg cecropin like Hp RpL1 2-20

FIG. 7 shows that increasing amounts of cecropin derived antimicrobial peptides do not effectively increase the pulsing effect.

Example 5

TRANSloading of Human Dendritic Cells with a MHC Class I and MHC class II Peptides by LL-37

To show that not only murine APCs but also human APCs are TRANSloaded by cathelicidin derived antimicrobial peptides, human CD1a positive (derived from human HLA-A2 positive donors, CD14+ positive PBMCs) dendritic cells were used as target APCs, and they were pulsed with a MHC class I binding peptide derived from influenza matrix protein A (amino acid residues 58-67, (Morrison, Elvin et al. 1992) or a MHC class II binding peptide derived from tetanus toxin (amino acid residues 830-843, (Valmori, Sabbatini et al. 1994). These two classes of antigenic fluorescein-tagged peptides were used. As cathelicidin derived antimicrobial peptide from human the known LL-37 (SEQ ID NO: 2) peptide (Cowland, Johnsen et al. 1995) was used.

The concentration of human cathelicidin derived antimicrobial peptide LL-37 and the antigenic peptides used are indicated as follows:

FIG. 8a
(1) no peptide (cells alone)
(2) 2.5 µg FL-GILGFVFTLT (SEQ ID NO:23) (MHC class I; peptide alone)
(3) 2.5 µg FL-GILGFVFTLT (SEQ ID NO:23) (MHC class I)+30 µg LL-37 (SEQ ID:2)

FIG. 8b
(1) no peptide (cells alone)
(2) 2.5 µg FL-QYIKANSKFIGITE (SEQ ID NO:24) (MHC class II; peptide alone)
(3) 2.5 µg FL-QYIKANSKFIGITE (SEQ ID NO:24) (MHC class II)+30 µg LL-37 (SEQ ID:2)

As shown in FIGS. 8a and 8b, the human cathelicidin derived antimicrobial peptide, LL-37 pulsed human dendritic cells with both classes (MHC class I & MHC class II) of antigenic peptide to a significant extent.

Thus, cathelicidin derived antimicrobial peptides from diverse species can serve as "carrier peptides" to pulse APCs of different origins.

Example 6

Testing the Ability to Enhance the Induction of Peptide Specific T Cells Responses In Vivo For testing the ability of these cathelicidin derived antimicrobial peptides to enhance the induction of peptide specific T cell responses in vivo, groups of 4 mice (C57BL/6, female, 8 weeks of age, H-2b) were injected subcutaneously into the flank 3 times (days 0, 7, and 14), by using a mixture of an antigenic melanoma peptide (100 µg) derived from TRP-2 (mouse tyrosinase related protein-2: amino acid sequence: 181-188; VYDFFVWL (SEQ ID NO:25)) (Bloom, Perry-Lalley et al. 1997) and diverse "carrier-peptides", either poly-L-arginine, murine cathelicidin derived antimicrobial peptide (SEQ ID NO:1) or bovine indolicidin (SEQ ID NO:3). The groups of mice were injected as follows (amounts indicated/per mouse).

(1) 100 µg VYDFFVWL (SEQ ID NO:25)
(2) 100 µg VYDFFVWL (SEQ ID NO:25)+100 µg poly-L-arginine
(3) 100µ VYDFFVWL (SEQ ID NO:25)+1000 µmurine cathelicidin derived antimicrobial peptide (SEQ ID NO:1)
(4) 100 µg VYDFFVWL (SEQ ID NO:25)+500 µg bovine indolicidin (SEQ ID NO:3)

Two weeks after the 3$^{rd}$ vaccination, draining (inguinal) lymph nodes and spleens were removed and lymph node cells. (FIG. 9) and splenocytes (FIG. 10) were activated ex vivo with TRP-2 derived (mouse tyrosinase related protein-2: aminoacid sequence 181-188: VYDFFVWL (SEQ ID NO:25) peptide to determine IFN-γ-producing specific cells in an ELISpot assay (number of IFN-γ ELISpots per million splenocytes and lymph node cells, respectively).

FIG. 9 shows that an injection of mice with peptide plus bovine indolicidin (SEQ ID NO:3) resulted in more IFN-γ-producing specific cells than an injection of mice only with peptide or with peptide plus poly-L-arginine.

FIG. 10 shows that both groups of mice injected with peptide plus bovine indolicidin (SEQ ID NO:3) and murine cathelicidin derived antimicrobial peptide (SEQ ID NO:1) had more IFN-γ-producing specific cells than mice injected only with peptide or with peptide plus poly-L-arginine.

This examples demonstrate clearly that cathelicidin derived antimicrobial peptides enhance the induction of peptide specific T cell responses in vivo.

In summary, all of the tested cathelicidin derived antimicrobial peptides showed a high "TRANSloading" and immunostimulating efficiency, indicating that cathelicidin derived antimicrobial peptides are able to pulse APCs with antigenic peptides in vitro and in vivo very efficiently and are good adjuvants/"carrier-peptides" for antigenic peptides in inducing adaptive immune responses.

REFERENCES

Agerberth, B., J. Charo, et al. (2000). "The human antimicrobial and chemotactic peptides LL-37 and alpha-defensins are expressed by specific lymphocyte and monocyte populations." *Blood* 96(9): 3086-3093.

Agerberth, B., J. Grunewald, et al. (1999). "Antibacterial components in bronchoalveolar lavage fluid from healthy individuals and sarcoidosis patients." *Am J Respir Crit Care Med* 160(1): 283-290.

Altschul, S. F., T. L. Madden, et al. (1997). "Gapped BLAST and PSI-BLAST: a new generation of protein database search programs." *Nucleic Acids Res* 25(17): 3389-3402.

Andreu, D. and L. Rivas (1998). "Animal antimicrobial peptides: an overview." *Biopolymers* 47(6): 415-433.

Bagella, L., M. Scocchi, et al. (1995). "cDNA sequences of three sheep myeloid cathelicidins." *FEBS Lett* 376(3): 225-228.

Bals, R., X. Wang, et al. (1998). "The peptide antibiotic LL-37/hCAP-18 is expressed in epithelia of the human lung where it has broad antimicrobial activity at the airway surface." *Proc Natl Acad Sci U S A* 95(16): 9541-9546.

Banchereau, J., F. Briere, et al. (2000). "Immunobiology of dendritic cells." *Annu Rev Immunol* 18: 767-811.

Banchereau, J. and R. M. Steinman (1998). "Dendritic cells and the control of immunity." *Nature* 392(6673): 245-252.

Basak, A., B. Ernst, et al. (1997). "Histidine-rich human salivary peptides are inhibitors of proprotein convertases furin and PC7 but act as substrates for PC1." *J Pept Res* 49(6): 596-603.

Befus, A. D., C. Mowat, et al. (1999). "Neutrophil defensins induce histamine secretion from mast cells: mechanisms of action." *J Immunol* 163(2): 947-953.

Bloom, M. B., D. Perry-Lalley, et al. (1997). "Identification of tyrosinase-related protein 2 as a tumor rejection antigen for the B16 melanoma." *J Exp Med* 185(3): 453-459.

Boman, H. G. (1991). "Antibacterial peptides: key components needed in immunity." *Cell* 65(2): 205-207.

Boman, H. G. (2000). "Innate immunity and the normal microflora." *Immunol Rev* 173: 5-16.

Bradbury, A. F. and D. G. Smyth (1991). "Peptide amidation." *Trends Biochem Sci* 16(3): 112-5.

Brossart, P. and M. J. Bevan (1997). "Presentation of exogenous protein antigens on major histocompatibility complex class I molecules by dendritic cells: pathway of presentation and regulation by cytokines." *Blood* 90(4): 1594-1599.

Buschle, e. a. M. (1998). "Chemically defined, cell-free cancer vaccines: use of tumor antigen-derived peptides or polyepitope proteins for vaccination." *Gene Therapy and molecular Biology* 1: 309-21.

Buschle, M., W. Schmidt, et al. (1997). "Transloading of tumor antigen-derived peptides into antigen-presenting cells." *Proc Natl Acad Sci U S A* 94(7): 3256-3261.

Chan, Y. R. and R. L. Gallo (1998). "PR-39, a syndecan-inducing antimicrobial peptide, binds and affects p 130 (Cas)." *J Biol Chem* 273(44): 28978-28985.

Chertov, O., D. F. Michiel, et al. (1996). "Identification of defensin-1, defensin-2, and CAP37/azurocidin as T-cell chemoattractant proteins released from interleukin-8-stimulated neutrophils." *J Biol Chem* 271(6): 2935-2940.

Cole, A. M., J. Shi, et al. (2001). "Inhibition of neutrophil elastase prevents cathelicidin activation and impairs clearance of bacteria from wounds." *Blood* 97(1): 297-304.

Cowland, J. B., A. H. Johnsen, et al. (1995). "hCAP-18, a cathelin/pro-bactenecin-like protein of human neutrophil specific granules." *FEBS Lett* 368(1): 173-176.

De, Y., Q. Chen, et al. (2000). "LL-37, the Neutrophil Granule- and Epithelial cell-derived Cathelicidin, Utilizes Formyl Peptide Receptor-like 1 (FPRL1) as a Receptor to Chemoattract Human Peripheral Blood Neutrophils, Monocytes, and T Cells." *J Exp Med* 192(7)-1069-1074.

Del Sal, G., P. Storici, et al. (1992). "cDNA cloning of the neutrophil bactericidal peptide indolicidin." *Biochem Biophys Res Commun* 187(1): 467-472.

Falla, T. J., D. N. Karunaratne, et al. (1996). "Mode of action of the antimicrobial peptide indolicidin." *J Biol Chem* 271 (32): 19298-19303.

Fallarino, F., C. Uyttenhove, et al. (1999). "Improved efficacy of dendritic cell vaccines and successful immunization with tumor antigen peptide-pulsed peripheral blood mononuclear cells by coadministration of recombinant murine interleukin-12." *Int J Cancer* 80(2): 324-333.

Frohm, M., B. Agerberth, et al. (1997). "The expression of the gene coding for the antibacterial peptide LL-37 is induced in human keratinocytes during inflammatory disorders." *J Biol Chem* 272(24): 15258-15263.

Frohm Nilsson, M., B. Sandstedt, et al. (1999). "The human cationic antimicrobial protein (hCAP18), a peptide antibiotic, is widely expressed in human squamous epithelia and colocalizes with interleukin-6." *Infect Immun* 67(5): 2561-2566.

Gallo, R. L., K. J. Kim, et al. (1997). "Identification of CRAMP, a cathelin-related antimicrobial peptide expressed in the embryonic and adult mouse." *J Biol Chem* 272(20): 13088-13093.

Gallo, R. L., M. Ono, et al. (1994). "Syndecans, cell surface heparan sulfate proteoglycans, are induced by a proline-rich antimicrobial peptide from wounds." *Proc Natl Acad Sci U S A* 91(23): 11035-11039.

Ganz, T. and R. I. Lehrer (1994). "Defensins." *Curr Opin Immunol* 6(4): 584-589.

Ganz, T. and R. I. Lehrer (1997). "Antimicrobial peptides of leukocytes." *Curr Opin Hematol* 4(1): 53-58.

Ganz, T. and R. I. Lehrer (1998). "Antimicrobial peptides of vertebrates." *Curr Opin Immunol* 10(1): 41-44.

Ganz, T. and R. I. Lehrer (1999). "Antibiotic peptides from higher eukaryotes: biology and applications." *Mol Med Today* 5(7): 292-297.

Garcia, J. R., A. Krause, et al. (2001). "Human beta-defensin 4: a novel inducible peptide with a specific salt-sensitive spectrum of antimicrobial activity." *Faseb J* 15(10): 1819-1821.

Gennaro, R., M. Scocchi, et al. (1998). "Biological characterization of a novel mammalian antimicrobial peptide." *Biochim Biophys Acta* 1425(2): 361-368.

Gough, M., R. E. Hancock, et al. (1996). "Antiendotoxin activity of cationic peptide antimicrobial agents." *Infect Immun* 64(12): 4922-4927.

Gudmundsson, G. H. and B. Agerberth (1999). "Neutrophil antibacterial peptides, multifunctional effector molecules in the mammalian immune system." *J Immunol Methods* 232(1-2): 45-54.

Gudmundsson, G. H., B. Agerberth, et al. (1996). "The human gene FALL39 and processing of the cathelin precursor to the antibacterial peptide LL-37 in granulocytes." *Eur J Biochem* 238(2): 325-332.

Hancock, R. E. (1999). "Host defence (cationic) peptides: what is their future clinical potential?" *Drugs* 57(4): 469-473.

Hancock, R. E. and G. Diamond (2000). "The role of cationic antimicrobial peptides in innate host defences." *Trends Microbiol* 8(9): 402-410.

Hancock, R. E. and M. G. Scott (2000). "The role of antimicrobial peptides in animal defenses." *Proc Natl Acad Sci U S A* 97(16): 8856-8861.

Harder, J., J. Bartels, et al. (2000). "Isolation and characterization of Human {beta}-Defensin-3, a novel human inducible peptide antibiotic." *J Biol Chem*.

Harding, C. (1995). "Phagocytic processing of antigens for presentation by MHC molecules." *Trends in Cell Biology* 5(3): 105-109.

Harding, C. (1996). "Class I MHC presentation of exogenous antigens." *J Clin Immunol* 16(2): 90-6.

Harwig, S. S., V. N. Kokryakov, et al. (1995). "Prophenin-1, an exceptionally proline-rich antimicrobial peptide from porcine leukocytes." *FEBS Lett.* 362(1): 65-69.

Higazi, A. A. R., T. Ganz, et al. (1996). "Defensin modulates tissue-type plasminogen activator and plasminogen binding to fibrin and endothelial cells." *J Biol Chem* 271(30): 17650-17655.

Kenney, R. T., D. L. Sacks, et al. (1999). "Protective immunity using recombinant human IL-12 and alum as adjuvants in a primate model of cutaneous leishmaniasis." *J Immunol* 163(8):4481-4488.

Kreil, G. (1997). "D-amino acids in animal peptides." *Annu Rev Biochem* 66: 337-345.

Kurts, C., W. R. Heath, et al. (1996). "Constitutive class I-restricted exogenous presentation of self antigens in vivo." *J Exp Med* 184(3):923-930.

Lehrer, R. I. and T. Ganz (1999). "Antimicrobial peptides in mammalian and insect host defence." *Curr Opin Immunol* 11(1):23-27.

Lehrer, R. I., A. K. Lichtenstein, et al. (1993). "Defensins: antimicrobial and cytotoxic peptides of mammalian cells." *Annu Rev Immunol* 11: 105-128.

Lillard, J. W., Jr., P. N. Boyaka, et al. (1999). "Mechanisms for induction of acquired host immunity by neutrophil peptide defensins." *Proc Natl Acad Sci U S A* 96(2):651-656.

Lindblad, E. B., M. J. Elhay, et al. (1997). "Adjuvant modulation of immune responses to tuberculosis subunit vaccines." *Infect Immun* 65(2):623-629.

Mahoney, M. M., A. Y. Lee, et al. (1995). "Molecular analysis of the sheep cathelin family reveals a novel antimicrobial peptide." *FEBS Lett* 377(3):519-522.

Malm, J., O. Sorensen, et al. (2000). "The human cationic antimicrobial protein (hCAP-18) is expressed in the epithelium of human epididymis, is present in seminal plasma at high concentrations, and is attached to spermatozoa." *Infect Immun* 68(7):4297-4302.

McWilliam, A. S., S. Napoli, et al. (1996). "Dendritic cells are recruited into the airway epithelium during the inflammatory response to a broad spectrum of stimuli." *J Exp Med* 184(6):2429-2432.

Mizukawa, N., K. Sugiyama, et al. (1999). "Presence of defensin in epithelial Langerhans cells adjacent to oral carcinomas and precancerous lesions." *Anticancer Res* 19(4B): 2969-2971.

Monaco, J. J. (1992). "A molecular model of MHC class-I-restricted antigen processing." *Immunol Today* 13(5):173-179.

Morrison, J., J. Elvin, et al. (1992). "Identification of the nonamer peptide from influenza A matrix protein and the role of pockets of HLA-A2 in its recognition by cytotoxic T lymphocytes." *Eur J Immunol* 22(4):903-907.

Murphy, P. M. (1994). "The molecular biology of leukocyte chemoattractant receptors." *Annu Rev Immunol* 12:593-633.

Niyonsaba, F., A. Someya, et al. (2001). "Evaluation of the effects of peptide antibiotics human beta-defensins-1/-2 and LL-37 on histamine release and prostaglandin D(2) production from mast cells." *Eur J Immunol* 31(4):1066-1075.

Popsueva, A. E., M. V. Zinovjeva, et al. (1996). "A novel murine cathelin-like protein expressed in bone marrow." *FEBS Lett* 391(1-2): 5-8.

Putsep, K., C. I. Branden, et al. (1999). "Antibacterial peptide from *H. pylori.*" *Nature* 398(6729):671-672.

Putsep, K., S. Normark, et al. (1999). "The origin of cecropins; implications from synthetic peptides derived from ribosomal protein L1." *FEBS Lett* 451(3):249-252.

Schijns, V. E. (2000). "Immunological concepts of vaccine adjuvant activity." *Curr Opin Immunol* 12(4):456-463.

Schmidt, W., M. Buschle, et al. (1997). "Cell-free tumor antigen peptide-based cancer vaccines." *Proc Natl Acad Sci U S A* 94(7):3262-3267.

Schonwetter, B. S., E. D. Stolzenberg, et al. (1995). "Epithelial antibiotics induced at sites of inflammation." *Science* 267(5204):1645-1648.

Scott, M. G., M. R. Gold, et al. (1999). "Interaction of cationic peptides with lipoteichoic acid and gram-positive bacteria." *Infect Immun* 67(12):6445-6453.

Scott, M. G., C. M. Rosenberger, et al. (2000). "An alpha-helical cationic antimicrobial peptide selectively modulates macrophage responses to lipopolysaccharide and directly alters macrophage gene expression." *J Immunol* 165(6):3358-3365.

Scott, M. G., H. Yan, et al. (1999). "Biological properties of structurally related alpha-helical cationic antimicrobial peptides." *Infect Immun* 67(4):2005-2009.

Selsted, M. E., M. J. Novotny, et al. (1992). "Indolicidin, a novel bactericidal tridecapeptide amide from neutrophils." *J Biol Chem* 267(7):4292-4295.

Singh, M. and D. O'Hagan (1999). "Advances in vaccine adjuvants." *Nat Biotechnol* 17(11):1075-1081.

Skerlavaj, B., R. Gennaro, et al. (1996). "Biological characterization of two novel cathelicidin-derived peptides and identification of structural requirements for their antimicrobial and cell lytic activities." *J Biol Chem* 271(45): 28375-28381.

Sorensen, O., K. Arnljots, et al. (1997). "The human antibacterial cathelicidin, hCAP-18, is synthesized in myelocytes and metamyelocytes and localized to specific granules in neutrophils." *Blood* 90(7):2796-2803.

Sorensen, O., T. Bratt, et al. (1999). "The human antibacterial cathelicidin, hCAP-18, is bound to lipoproteins in plasma." *J Biol Chem* 274(32):22445-22451.

Sorensen, O. E., P. Follin, et al. (2001). "Human cathelicidin, hCAP-18, is processed to the antimicrobial peptide LL-37 by extracellular cleavage with proteinase 3." *Blood* 97(12): 3951-3959.

Steinman, R. M. (1991). "The dendritic cell system and its role in immunogenicity." *Annu Rev Immunol* 9:271-296.

Storici, P., A. Tossi, et al. (1996). "Purification and structural characterization of bovine cathelicidins, precursors of antimicrobial peptides." *Eur J Biochem* 238(3):769-776.

Tani, K., W. J. Murphy, et al. (2000). "Defensins act as potent adjuvants that promote cellular and humoral immune responses in mice to a lymphoma idiotype and carrier antigens." *Int Immunol* 12(5):691-700.

Travis, S. M., N. N. Anderson, et al. (2000). "Bactericidal activity of mammalian cathelicidin-derived peptides." *Infect Immun* 68(5):2748-2755.

Valmori, D., A. Sabbatini, et al. (1994). "Functional analysis of two tetanus toxin universal T cell epitopes in their interaction with DR1101 and DR1104 alleles." *J Immunol* 152 (6): 2921-2929.

Van Wetering, S., S. P. Mannesse-Lazeroms, et al. (1997). "Effect of neutrophil serine proteinases and defensins on lung epithelial cells: modulation of cytotoxicity and IL-8 production." *J Leukoc Biol* 62(2):217-226.

Van Wetering, S., S. P. Mannesse-Lazeroms, et al. (1997). "Effect of defensins on interleukin-8 synthesis in airway epithelial cells." *Am J Physiol* 272(5 Pt 1): L888-896.

Wilson, C. L., A. J. Ouellette, et al. (1999). "Regulation of intestinal alpha-defensin activation by the metalloproteinase matrilysin in innate host defense." *Science* 286(5437): 113-117.

Yang, D., Q. Chen, et al. (2000). "Human neutrophil defensins selectively chemoattract naive T and immature dendritic cells." *J Leukoc Biol* 68(1):9-14.

Yang, D., Q. Chen, et al. (2001). "Differential regulation of formyl peptide receptor-like 1 expression during the differentiation of monocytes to dendritic cells and macrophages." *J Immunol* 166(6):4092-4098.

Yang, D., O. Chertov, et al. (1999). "Beta-defensins: linking innate and adaptive immunity through dendritic and T cell CCR6." *Science* 286(5439):525-528.

Zanetti, M., R. Gennaro, et al. (1995). "Cathelicidins: a novel protein family with a common proregion and a variable C-terminal antimicrobial domain." *FEBS Lett* 374(1):1-5.

Zanetti, M., R. Gennaro, et al. (1997). "The cathelicidin family of antimicrobial peptide precursors: a component of the oxygen-independent defense mechanisms of neutrophils." *Ann N Y Acad Sci* 832:147-162.

Zanetti, M., R. Gennaro, et al. (2000). "Structure and biology of cathelicidins." *Adv Exp Med Biol* 479:203-218.

Zinkernagel, R. M., S. Ehl, et al. (1997). "Antigen localisation regulates immune responses in a dose- and time-dependent fashion: a geographical view of immune reactivity." *Immunol Rev* 156:199-209.

The invention claimed is:

1. A method of enhancing an immune response to an antigen comprising:
obtaining a composition comprising an antigen and a cathelicidin-derived antimicrobial peptide having up to 60 amino acids and comprising the amino acid sequence of SEQ ID NO: 1, SEQ ID NO: 2, SEQ ID NO: 3, SEQ ID NO: 4, SEQ ID NO: 12, SEQ ID NO: 13, SEQ ID NO: 14, SEQ ID NO: 15, SEQ ID NO: 16, SEQ ID NO: 17, SEQ ID NO: 18, or SEQ ID NO: 19; and
administering the composition to a human to enhance an immune response to the antigen, wherein the antigen is a protein or peptide derived from a pathogen.

2. The method of claim 1, wherein the cathelicidin-derived antimicrobial peptide enhances the uptake of the antigen in antigen presenting cells (APC).

3. The method of claim 1, further comprising administering at least one further immune response stimulating substance to the human.

4. The method of claim 3, wherein the immune response stimulating substance is a cytokine.

5. The method of claim 3, wherein the immune response stimulating substance is aluminum hydroxide.

6. The method of claim 3, wherein the immune response stimulating substance is a polylysine or a polyarginine.

* * * * *